(12) United States Patent
Zhang et al.

(10) Patent No.: US 7,618,945 B2
(45) Date of Patent: Nov. 17, 2009

(54) HETEROARYL PEPTIDOMIMETICS AS THROMBIN RECEPTOR ANTAGONISTS

(75) Inventors: Han-Cheng Zhang, Lansdale, PA (US); Bruce E. Maryanoff, Forest Grove, PA (US); William J. Hoekstra, Chapel Hill, NC (US); Kimberly White, North Wales, PA (US)

(73) Assignee: Janssen Pharmaceutica, N.V. (BE)

( * ) Notice: Subject to any disclaimer, the term of this patent is extended or adjusted under 35 U.S.C. 154(b) by 171 days.

(21) Appl. No.: 11/227,504

(22) Filed: Sep. 15, 2005

(65) Prior Publication Data
US 2006/0009396 A1 Jan. 12, 2006

Related U.S. Application Data

(62) Division of application No. 10/732,701, filed on Dec. 10, 2003, now abandoned.

(60) Provisional application No. 60/436,130, filed on Dec. 23, 2002.

(51) Int. Cl.
*A61K 38/00* (2006.01)
*A61K 38/06* (2006.01)

(52) U.S. Cl. .......................... 514/18; 530/331

(58) Field of Classification Search .................. None
See application file for complete search history.

(56) References Cited

U.S. PATENT DOCUMENTS

| 6,365,617 | B1 | 4/2002 | McComsey et al. | |
| 6,858,577 | B1 * | 2/2005 | Zhang et al. ............. | 514/2 |
| 7,183,252 | B2 * | 2/2007 | Zhang et al. ............. | 514/2 |
| 2002/0103138 | A1 | 8/2002 | D'Andrea et al. | |
| 2003/0224999 | A1 | 12/2003 | Zhang et al. | |
| 2004/0063642 | A1 | 4/2004 | Zhang et al. | |
| 2004/0138141 | A1 | 7/2004 | Zhang et al. | |

FOREIGN PATENT DOCUMENTS

| WO | WO 01/00576 A1 | 1/2001 |
| WO | WO 01/00656 A2 | 1/2001 |
| WO | WO 01/00657 A2 | 1/2001 |
| WO | WO 01/00659 A1 | 1/2001 |

OTHER PUBLICATIONS

Andrade-Gordon, et al., "Design Synthesis, and biological characterization of a peptide-mimetic antagonist for a tethered-ligand receptor," Proceedings of the National Academy of Science, 96(22): 12257-12262 (1999).
Vu, et al., Cell, 64: 1057-1068 (1991).
Nystedt, et al., Proceedings of the National Academy of Science, 91: 9208-9212 (1994).
Ishihara, et al., Nature, 386: 502-502 (1997).
Xu, et al., Proceedings of the National Academy of Science, 95: 6642-6646 (1998).
Cook, et al., Circulation, 91: 2961-2971 (1995).
Sugama, et al., Journal of Cell Biology, 119: 935-944 (1992).
Hung, et al., Journal of Cell Biology, 116: 827-832 (1992).
Tatakis, et al., Biochemical and Biophysical Research Communication, 174: 181-184 (1991).
Jalink, et al., Journal of Cell Biology, 118: 411-419 (1992).
Zhang, et al., Bioorganic Medicine Chemistry Letters, 11: 2105-2109 (2001).
Zhang, et al., Journal of Medical Chemistry, 44: 1021-1024 (2001).
Buchi, et al., Journal of American Chemical Society, 198: 4115-4119 (1986).
Jones, et al., Biochim. Biophys. Acta., 1136: 272-282 (1992).
PCT Search Report from International Application No. PCT/US03/39091 and dated Jul. 30, 2004.
Cabrera et al. Dynamic ordering of aggregated mesomorphic macromolecules Nature (London, United Kingdom) 1987, vol. 326, No. 6113, pp. 582-585.

* cited by examiner

*Primary Examiner*—Cecilia Tsang
*Assistant Examiner*—Marcela M Cordero Garcia

(57) ABSTRACT

The invention is directed to novel heteroaryl peptidomimetic compounds which are useful as thrombin receptor antagonists for the treatment of diseases associated with thrombosis, restenosis, hypertension, heart failure, arrhythmia, inflammation, angina, stroke, atherosclerosis, ischemic conditions, angiogenesis and related disorders, cancer, and neurodegenerative disorders. Pharmaceutical compositions comprising the substituted heteroaryl peptidomimetics of the present invention and methods of treating conditions mediated by the thrombin receptor are also disclosed.

3 Claims, No Drawings

HETEROARYL PEPTIDOMIMETICS AS THROMBIN RECEPTOR ANTAGONISTS

This application is a divisional of U.S. patent application Ser. No. 10/732,701, filed 10 Dec. 2003, now abandoned, which claims the benefit of U.S. Provisional Application No. 60/436,130, filed 23 Dec. 2002, the entire contents of which are incorporated herein in their entirety.

FIELD OF THE INVENTION

This invention relates to certain novel thrombin receptor antagonists, their synthesis and their use for the treatment of diseases associated with thrombosis, restenosis, hypertension, heart failure, arrhythmia, inflammation, angina, stroke, atherosclerosis, ischemic conditions, angiogenesis and related disorders, cancer, and neurodegenerative disorders.

BACKGROUND OF THE INVENTION

Thrombin is an important serine protease in hemostasis and thrombosis. One of the key actions of thrombin is cellular modulation via receptor activation. A functional human thrombin receptor (PAR-1), cloned by Coughlin in 1991 (T.-K. Vu, *Cell* 1991, 64, 1057), was found to be a member of the G-protein coupled receptor (GPCR) superfamily. The receptor activation putatively occurs by N-terminal recognition and proteolytic cleavage at the Arg-41/Ser-42 peptide bond to reveal a truncated N-terminus. This new receptor sequence can trigger activation and signal transduction leading to platelet aggregation. Since 1991, three other protease-activated receptors with extensive homology to the thrombin receptor, "PAR-2" (S. Nystedt, *Proc. Natl. Acad. Sci USA* 1994, 91, 9208), "PAR-3" (H. Ishihara, *Nature* 1997, 386, 502), and "PAR-4" (W.-F. Xu, *Proc. Natl. Acad. Sci USA* 1998, 95, 6642), have been cloned. Thrombin receptor (PAR-1) specific antibody-induced blockade of the platelet thrombin receptor has shown efficacy against arterial thrombosis in vivo (J. J. Cook *Circulation* 1995, 91, 2961). Hence, antagonists of the thrombin receptor (PAR-1) are useful to block these protease-activated receptors and, as such, may be used to treat platelet mediated thrombotic disorders such as myocardial infarction, stroke, restenosis, angina, atherosclerosis, and ischemic conditions.

The thrombin receptor (PAR-1) has also been identified on other cell types: endothelial, fibroblast, renal, osteosarcoma, smooth muscle, myocytes, tumor, and neuronal/glia. Thrombin activation of endothelial cells upregulates P-selectin to induce polymorphonuclear leukocyte adhesion—an inflammatory response of the vessel wall (Y. Sugama, J. Cell Biol. 1992, 119, 935). In fibroblasts, thrombin receptor (PAR-1) activation induces proliferation and transmission of mitogenic signals (D. T. Hung, *J. Cell Biol.* 1992, 116, 827). Thrombin has been implicated in osteoblast proliferation through its activation of osteoblast cells (D. N. Tatakis, *Biochem. Biophys. Res. Commun.* 1991, 174, 181). Thrombin has been implicated in the regulation and retraction of neurons (K. Jalink, *J. Cell. Biol.* 1992, 118, 411). Therefore, in this context, the antagonist compounds of this invention may also be useful against inflammation, osteoporosis, angiogenesis and related disorders, cancer, neurodegenerative disorders, hypertension, heart failure, arrhythmia, glomerulonephritis.

In International Patent Application WO 01/00576, indole and indazole urea peptoids are disclosed as thrombin receptor antagonists. The general structure of the compounds disclosed is:

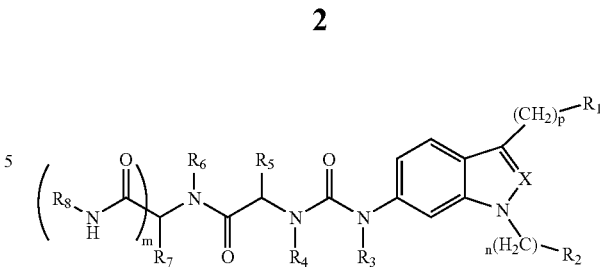

In International Patent Application WO 01/00656, novel indazole peptidomimetic compounds are disclosed as thrombin receptor antagonists. The general structure of the compounds disclosed is:

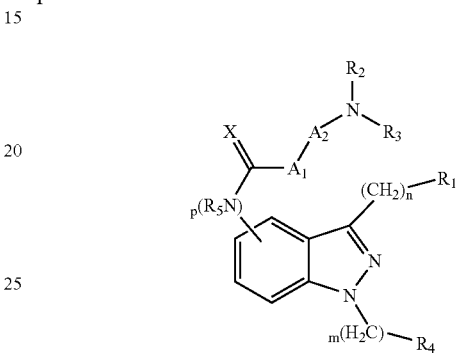

In International Patent Application WO 01/00657, novel indole peptidomimetic compounds are disclosed as thrombin receptor antagonists. The general structure of the compounds disclosed is:

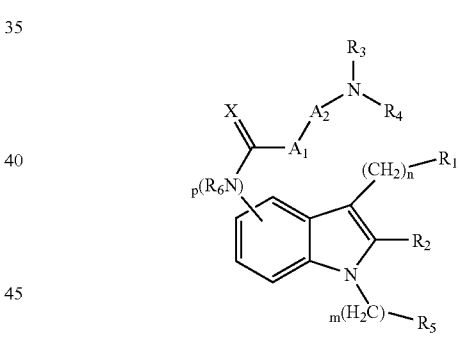

In International Patent Application WO 01/00659, novel benzimidazolone peptidomimetic compounds are disclosed as thrombin receptor antagonists. The general structure of the compounds disclosed is:

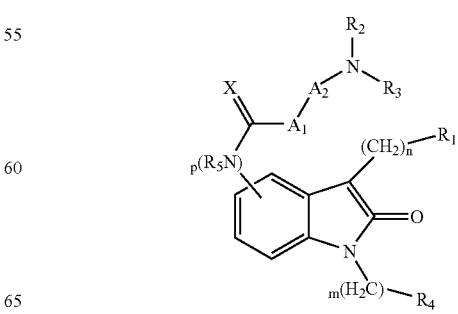

The indole-based petide mimetics disclosed in the above international applications are also described in Zhang, H-C et. al. *Bioorg. Med. Chem. Lett.* 2001, 11, 2105-2109.

Similarly, the indole and indazole based compounds disclosed in the above international applications are also described as thrombin receptor antagonists in Zhang, H-C et. al. *J. Med. Chem.* 2001, 44, 1021-1024.

The compounds of the present invention are a structurally novel class of heteroaryl peptidomimetics represented by the general formula (I) below.

SUMMARY OF THE INVENTION

The present invention is directed to structurally novel compounds represented by the following general formula (I):

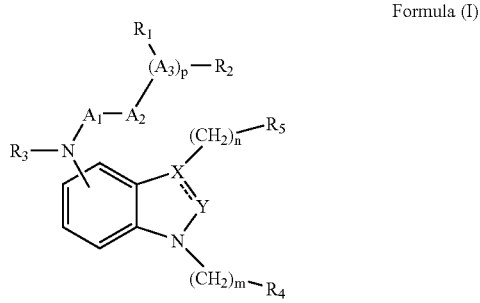

Formula (I)

wherein $A_1$, $A_2$ and $A_3$ are each independently a D- or L-amino acid selected from the group consisting of alanine, β-alanine, arginine, homoarginine, cyclohexylalanine, citrulline, cysteine (optionally substituted with $C_1$-$C_4$alkyl, aryl, or ar$C_1$-$C_4$alkyl), 2,4-diaminobutyric acid (optionally substituted with acyl, $C_1$-$C_4$alkyl, aroyl, amidino, or MeC(NH)—), 2,3 diaminopropionic acid (optionally substituted with acyl, $C_1$-$C_4$alkyl, aroyl, amidino, or MeC(NH)—), glutamine, glycine, indanylglycine, lysine (optionally substituted with acyl, $C_1$-$C_4$alkyl, aroyl, MeC(NH)—), valine, methionine, proline, serine (optionally substituted with $C_1$-$C_4$alkyl, aryl, or ar$C_1$-$C_4$alkyl), homoserine (optionally substituted with $C_1$-$C_4$alkyl, aryl, or ar$C_1$-$C_4$alkyl), tetrahydroisoquinoline-3-COOH, threonine (optionally substituted with $C_1$-$C_4$alkyl, aryl, or ar$C_1$-$C_4$alkyl), ornithine (optionally substituted with acyl, $C_1$-$C_4$alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

$R_1$ and $R_2$ are each independently selected from hydrogen, $C_1$-$C_8$alkyl, ar($C_1$-$C_8$)alkyl, $C_1$-$C_8$alkoxycarbonyl, aryloxycarbonyl, ar($C_1$-$C_8$)alkoxycarbonyl, $C_1$-$C_8$alkylcarbonyl, arylcarbonyl, ar($C_1$-$C_8$)alkylcarbonyl, aminocarbonyl, $C_1$-$C_8$alkylaminocarbonyl, $C_1$-$C_8$dialkylaminocarbonyl, arylaminocarbonyl, diarylaminocarbonyl, ar($C_1$-$C_8$)alkylaminocarbonyl, diar($C_1$-$C_8$)alkylaminocarbonyl, heterocyclylcarbonyl, heteroaryl($C_1$-$C_8$)alkyl, heteroaryloxycarbonyl, heteroaryl($C_1$-$C_8$)alkoxycarbonyl, heteroarylcarbonyl, heteroaryl($C_1$-$C_8$)alkylcarbonyl, heteroarylaminocarbonyl, diheteroarylaminocarbonyl, and heteroaryl($C_1$-$C_8$)alkylaminocarbonyl, diheteroaryl($C_1$-$C_8$)alkylaminocarbonyl wherein said aryl, ar($C_1$-$C_8$)alkyl, heteroaryl and heteroaryl ($C_1$-$C_8$)alkyl are optionally substituted with one or more of halogen, $C_1$-$C_8$alkyl, $C_1$-$C_8$alkoxy, hydroxy, cyano, amino, and nitro; $R_1$ and $R_2$ are covalently bonded to the N-terminus of $A_3$ when p is 1 or $A_2$ when p is 0;

Preferably $R_1$ is hydrogen;

Preferably, $R_2$ is selected from hydrogen, $C_1$-$C_8$alkyl, aryloxycarbonyl, ar($C_1$-$C_8$)alkoxycarbonyl, $C_1$-$C_8$alkoxycarbonyl, $C_1$-$C_8$alkylcarbonyl, ar($C_1$-$C_8$)alkylcarbonyl, arylaminocarbonyl, diarylaminocarbonyl, $C_1$-$C_8$alkylaminocarbonyl, $C_1$-$C_8$dialkylaminocarbonyl, ar($C_1$-$C_8$alkoxy)carbonyl, and heterocyclylcarbonyl;

$R_3$ is selected from hydrogen or $C_1$-$C_8$alkyl; preferably, $R_3$ is hydrogen;

$R_4$ is selected from unsubstituted or substituted aryl, ar$C_1$-$C_8$alkyl, $C_3$-$C_8$cycloalkyl, heteroaryl, or heteroaryl($C_1$-$C_8$) alkyl, where the substituents on the aryl, ar$C_1$-$C_8$alkyl, cycloalkyl, heteroaryl or heteroaryl($C_1$-$C_8$)alkyl group are independently selected from one or more of halogen, nitro, amino, cyano, hydroxyalkyl, $C_1$-$C_8$alkyl, $C_1$-$C_8$alkoxy, hydroxy, $C_1$-$C_4$alkylcarbonyl, $C_1$-$C_8$alkoxycarbonyl, fluorinated $C_1$-$C_4$alkyl, fluorinated $C_1$-$C_4$alkoxy or $C_1$-$C_4$alkylsulfonyl;

Preferably, $R_4$ is selected from unsubstituted or substituted aryl, ar$C_1$-$C_6$alkyl, $C_3$-$C_6$cycloalkyl or heteroaryl, where the substituents on the aryl, aralkyl, cycloalkyl or heteroaryl group are independently selected from one to three substituents selected from halogen, cyano, $C_1$-$C_4$alkyl, $C_1$-$C_4$alkoxy, $C_1$-$C_4$ alkoxycarbonyl, fluorinated $C_1$-$C_4$alkyl, fluorinated $C_1$-$C_4$alkoxy or $C_1$-$C_4$alkylsulfonyl;

$R_5$ is selected from amino, $C_1$-$C_8$alkylamino, $C_1$-$C_8$dialkylamino, arylamino, ar$C_1$-$C_8$alkylamino, $C_3$-$C_8$cycloalkylamino, heteroalkyl$C_1$-$C_8$alkylamino, heteroalkyl$C_1$-$C_8$alkyl-N-methylamino, $C_1$-$C_8$dialkylamino ($C_1$-$C_8$)alkylamino, —N($C_1$-$C_8$alkyl)-$C_1$-$C_8$alkyl-N($C_1$-$C_8$alkyl)$_2$, —N($C_1$-$C_8$alkyl)($C_1$-$C_8$alkenyl), —N($C_1$-$C_8$alkyl)($C_3$-$C_8$cycloalkyl), heteroalkyl or substituted heteroalkyl wherein the substituent on the heteroalkyl is selected from oxo, amino, $C_1$-$C_8$alkoxy($C_1$-$C_8$)alkyl, $C_1$-$C_8$alkylamino or $C_1$-$C_8$dialkylamino;

Preferably, $R_5$ is selected from amino, $C_1$-$C_6$alkylamino, $C_1$-$C_6$ dialkylamino, $C_3$-$C_8$cycloalkylamino, arylamino, ar$C_1$-$C_6$alkylamino, heteroalkyl$C_1$-$C_6$alkylamino, —N($C_1$-$C_6$alkyl)-$C_1$-$C_6$alkyl-N($C_1$-$C_6$alkyl)$_2$, heteroalkyl or substituted heteroalkyl wherein the substituent on the heteroalkyl is selected from oxo, amino, $C_1$-$C_6$alkoxy$C_1$-$C_6$ alkyl, $C_1$-$C_6$alkylamino or $C_1$-$C_6$ dialkylamino;

X is N or C;

Y is N, C or —CO—;

Provided that when Y is N, then X is C and there is a double bond between X and Y; Provided also that when Y is C, then X is C and there is a double bond between X and Y; And provided also that when Y is —CO—, then X is N and there is a single bond between X and Y;

m is an integer selected from 0, 1, 2 or 3;

n is an integer selected from 1 or 2;

p is an integer selected from 0 or 1; preferably, p is 0;

preferably, the point of attachment of —N($R_3$)-$A_1$-$A_2$-($A_3$)$_p$-$R_1$($R_2$) is the 5 or 6 position of the core heterocyclic ring; more preferably, the point of attachment is the 6 position; and enantiomers, diastereomers, tautomers, solvates, and pharmaceutically acceptable salts thereof.

A preferred embodiment of the present invention is directed to structurally novel compounds represented by the following general formula (II):

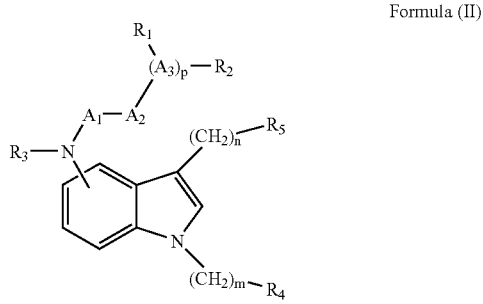

Formula (II)

wherein $A_1$, $A_2$ and $A_3$ are each independently a D- or L-amino acid selected from the group consisting of alanine, β-alanine, arginine, homoarginine, cyclohexylalanine, citrulline, cysteine (optionally substituted with $C_1$-$C_4$alkyl, aryl, or ar$C_1$-$C_4$alkyl), 2,4-diaminobutyric acid (optionally substituted with acyl, $C_1$-$C_4$alkyl, aroyl, amidino, or MeC(NH)—), 2,3 diaminopropionic acid (optionally substituted with acyl, $C_1$-$C_4$alkyl, aroyl, amidino, or MeC(NH)—), glutamine, glycine, indanylglycine, lysine (optionally substituted with acyl, $C_1$-$C_4$alkyl, aroyl, MeC(NH)—), valine, methionine, proline, serine (optionally substituted with $C_1$-$C_4$alkyl, aryl, or ar$C_1$-$C_4$alkyl), homoserine (optionally substituted with $C_1$-$C_4$alkyl, aryl, or ar$C_1$-$C_4$alkyl), tetrahydroisoquinoline-3-COOH, threonine (optionally substituted with $C_1$-$C_4$alkyl, aryl, or ar$C_1$-$C_4$alkyl), ornithine (optionally substituted with acyl, $C_1$-$C_4$alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

$R_1$ and $R_2$ are each independently selected from hydrogen, $C_1$-$C_8$alkyl, ar($C_1$-$C_8$)alkyl, $C_1$-$C_8$alkoxycarbonyl, aryloxycarbonyl, ar($C_1$-$C_8$)alkoxycarbonyl, $C_1$-$C_8$alkylcarbonyl, arylcarbonyl, ar($C_1$-$C_8$)alkylcarbonyl, aminocarbonyl, $C_1$-$C_8$alkylaminocarbonyl, $C_1$-$C_8$dialkylaminocarbonyl, arylaminocarbonyl, diarylaminocarbonyl, ar($C_1$-$C_8$)alkylaminocarbonyl, diar($C_1$-$C_8$)alkylaminocarbonyl, heterocyclylcarbonyl, heteroaryl($C_1$-$C_8$)alkyl, heteroaryloxycarbonyl, heteroaryl($C_1$-$C_8$)alkoxycarbonyl, heteroarylcarbonyl, heteroaryl($C_1$-$C_8$)alkylcarbonyl, heteroarylaminocarbonyl, diheteroarylaminocarbonyl, heteroaryl($C_1$-$C_8$)alkylaminocarbonyl, and diheteroaryl($C_1$-$C_8$)alkylaminocarbonyl, wherein said aryl, ar($C_1$-$C_8$)alkyl, heteroaryl and heteroaryl ($C_1$-$C_8$)alkyl are optionally substituted with one or more of halogen, $C_1$-$C_8$alkyl, $C_1$-$C_8$alkoxy hydroxy, cyano, amino, and nitro; $R_1$ and $R_2$ are covalently bonded to the N-terminus of $A_3$ when p is 1 or $A_2$ when p is 0;

Preferably, $R_1$ is hydrogen;

Preferably, $R_2$ is selected from hydrogen, $C_1$-$C_8$alkyl, aryloxycarbonyl, ar($C_1$-$C_8$)alkoxycarbonyl, $C_1$-$C_8$alkoxycarbonyl, $C_1$-$C_8$alkylcarbonyl, ar($C_1$-$C_8$)alkylcarbonyl, arylaminocarbonyl, diarylaminocarbonyl, $C_1$-$C_8$alkylaminocarbonyl, $C_1$-$C_8$dialkylaminocarbonyl, ar($C_1$-$C_8$alkoxy)carbonyl, and heterocyclylcarbonyl;

$R_3$ is selected from hydrogen or $C_1$-$C_8$ alkyl; preferably, $R_3$ is hydrogen;

$R_4$ is selected from unsubstituted or substituted aryl, ar$C_1$-$C_8$alkyl, $C_3$-$C_8$cycloalkyl, heteroaryl, or heteroaryl($C_1$-$C_8$) alkyl, where the substituents on the aryl, ar$C_1$-$C_8$alkyl, cycloalkyl, heteroaryl or heteroaryl($C_1$-$C_8$)alkyl, group are independently selected from one or more of halogen, nitro, amino, cyano, hydroxyalkyl, $C_1$-$C_8$alkyl, $C_1$-$C_8$alkoxy, hydroxy, $C_1$-$C_4$alkylcarbonyl, $C_1$-$C_8$alkoxycarbonyl, fluorinated $C_1$-$C_4$alkyl, fluorinated $C_1$-$C_4$alkoxy or $C_1$-$C_4$alkylsulfonyl;

Preferably, $R_4$ is selected from unsubstituted or substituted aryl, ar$C_1$-$C_6$alkyl, $C_3$-$C_6$cycloalkyl or heteroaryl, where the substituents on the aryl, aralkyl, cycloalkyl or heteroaryl group are independently selected from one to three substituents selected from halogen, cyano, $C_1$-$C_4$alkyl, $C_1$-$C_4$alkoxy, $C_1$-$C_4$ alkoxycarbonyl, fluorinated $C_1$-$C_4$alkyl, fluorinated $C_1$-$C_4$alkoxy or $C_1$-$C_4$alkylsulfonyl;

$R_5$ is selected from amino, $C_1$-$C_8$alkylamino, $C_1$-$C_8$dialkylamino, arylamino, ar$C_1$-$C_8$alkylamino, $C_3$-$C_8$cycloalkylamino, heteroalkyl$C_1$-$C_8$alkylamino, heteroalkyl$C_1$-$C_8$alkyl-N-methylamino, $C_1$-$C_8$dialkylamino ($C_1$-$C_8$)alkylamino, —N($C_1$-$C_8$alkyl)-$C_1$-$C_8$alkyl-N($C_1$-$C_8$alkyl)$_2$, —N($C_1$-$C_8$alkyl)($C_1$-$C_8$alkenyl), —N($C_1$-$C_8$alkyl)($C_3$-$C_8$cycloalkyl), heteroalkyl or substituted heteroalkyl wherein the substituent on the heteroalkyl is selected from oxo, amino, $C_1$-$C_8$alkoxy($C_1$-$C_8$)alkyl, $C_1$-$C_8$alkylamino or $C_1$-$C_8$dialkylamino;

Preferably, $R_5$ is selected from amino, $C_1$-$C_6$alkylamino, $C_1$-$C_6$dialkylamino, $C_3$-$C_8$cycloalkylamino, arylamino, ar$C_1$-$C_6$alkylamino, heteroalkyl$C_1$-$C_6$alkylamino, —N($C_1$-$C_6$alkyl)-$C_1$-$C_6$alkyl-N($C_1$-$C_6$alkyl)$_2$, heteroalkyl or substituted heteroalkyl wherein the substituent on the heteroalkyl is selected from oxo, amino, $C_1$-$C_6$alkoxy$C_1$-$C_6$ alkyl, $C_1$-$C_6$alkylamino or $C_1$-$C_6$dialkylamino;

m is an integer selected from 0, 1, 2 or 3;

n is an integer selected from 1 or 2;

p is an integer selected from 0 or 1; preferably, p is 0;

preferably, the point of attachment of —N($R_3$)-$A_1$-$A_2$-($A_3$)$_p$-$R_1$($R_2$) is the 5 or 6 position of the core heterocyclic ring; more preferably, the point of attachment is the 6 position; and enantiomers, diastereomers, tautomers, solvates, and pharmaceutically acceptable salts thereof.

Another preferred embodiment of the present invention is directed to structurally novel compounds represented by the following general formula (III):

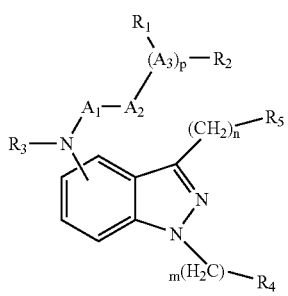

Formula (III)

wherein $A_1$, $A_2$ and $A_3$ are each independently a D- or L-amino acid selected from the group consisting of alanine, β-alanine, arginine, homoarginine, cyclohexylalanine, citrulline, cysteine (optionally substituted with $C_1$-$C_4$alkyl, aryl, or ar$C_1$-$C_4$alkyl), 2,4-diaminobutyric acid (optionally substituted with acyl, $C_1$-$C_4$alkyl, aroyl, amidino, or MeC(NH)—), 2,3 diaminopropionic acid (optionally substituted with acyl, $C_1$-$C_4$alkyl, aroyl, amidino, or MeC(NH)—), glutamine, glycine, indanylglycine, lysine (optionally substituted with acyl, $C_1$-$C_4$alkyl, aroyl, MeC(NH)—), valine, methionine, proline, serine (optionally substituted with $C_1$-$C_4$alkyl, aryl, or ar$C_1$-$C_4$alkyl), homoserine (optionally substituted with $C_1$-$C_4$alkyl, aryl, or ar$C_1$-$C_4$alkyl), tetrahydroisoquinoline-3-COOH, threonine (optionally substituted with $C_1$-$C_4$alkyl, aryl, or ar$C_1$-$C_4$alkyl), ornithine (optionally substituted with acyl, $C_1$-$C_4$alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

$R_1$ and $R_2$ are each independently selected from hydrogen, $C_1$-$C_8$alkyl, ar($C_1$-$C_8$)alkyl, $C_1$-$C_8$alkoxycarbonyl, aryloxycarbonyl, ar($C_1$-$C_8$)alkoxycarbonyl, $C_1$-$C_8$alkylcarbonyl, arylcarbonyl, ar($C_1$-$C_8$)alkylcarbonyl, aminocarbonyl, $C_1$-$C_8$alkylaminocarbonyl, $C_1$-$C_8$dialkylaminocarbonyl, arylaminocarbonyl, diarylaminocarbonyl, ar($C_1$-$C_8$)alkylaminocarbonyl, diar($C_1$-$C_8$)alkylaminocarbonyl, heterocyclylcarbonyl, heteroaryl($C_1$-$C_8$)alkyl, heteroaryloxycarbonyl, heteroaryl($C_1$-$C_8$)alkoxycarbonyl, heteroarylcarbonyl, heteroaryl($C_1$-$C_8$)alkylcarbonyl, heteroarylaminocarbonyl, diheteroarylaminocarbonyl, heteroaryl($C_1$-$C_8$)alkylaminocarbonyl, and diheteroaryl($C_1$-$C_8$)alkylaminocarbonyl, wherein said aryl, ar($C_1$-$C_8$)alkyl, heteroaryl and heteroaryl ($C_1$-$C_8$)alkyl are optionally substituted with one or more of halogen, $C_1$-$C_8$alkyl, $C_1$-$C_8$alkoxy hydroxy, cyano, amino, and nitro; $R_1$ and $R_2$ are covalently bonded to the N-terminus of $A_3$ when p is 1 or $A_2$ when p is 0;

Preferably, $R_1$ is hydrogen;

Preferably, $R_2$ is selected from hydrogen, $C_1$-$C_8$alkyl, aryloxycarbonyl, ar($C_1$-$C_8$)alkoxycarbonyl, $C_1$-$C_8$alkoxycarbonyl, $C_1$-$C_8$alkylcarbonyl, ar($C_1$-$C_8$)alkylcarbonyl, arylaminocarbonyl, diarylaminocarbonyl, $C_1$-$C_8$alkylaminocarbonyl, $C_1$-$C_8$dialkylaminocarbonyl, ar($C_1$-$C_8$alkoxy)carbonyl, and heterocyclylcarbonyl;

$R_3$ is selected from hydrogen or $C_1$-$C_8$ alkyl; preferably, $R_3$ is hydrogen;

$R_4$ is selected from unsubstituted or substituted aryl, ar$C_1$-$C_8$alkyl, $C_3$-$C_8$cycloalkyl, heteroaryl, or heteroaryl($C_1$-$C_8$) alkyl, where the substituents on the aryl, ar$C_1$-$C_8$alkyl, cycloalkyl, heteroaryl or heteroaryl($C_1$-$C_8$)alkyl, group are independently selected from one or more of halogen, nitro, amino, cyano, hydroxyalkyl, $C_1$-$C_8$alkyl, $C_1$-$C_8$alkoxy, hydroxy, $C_1$-$C_4$alkylcarbonyl, $C_1$-$C_8$alkoxycarbonyl, fluorinated $C_1$-$C_4$alkyl, fluorinated $C_1$-$C_4$alkoxy or $C_1$-$C_4$alkylsulfonyl;

Preferably, $R_4$ is selected from unsubstituted or substituted aryl, ar$C_1$-$C_6$alkyl, $C_3$-$C_6$cycloalkyl or heteroaryl, where the substituents on the aryl, aralkyl, cycloalkyl or heteroaryl group are independently selected from one to three substituents selected from halogen, cyano, $C_1$-$C_4$alkyl, $C_1$-$C_4$alkoxy, $C_1$-$C_4$ alkoxycarbonyl, fluorinated $C_1$-$C_4$alkyl, fluorinated $C_1$-$C_4$alkoxy or $C_1$-$C_4$alkylsulfonyl;

$R_5$ is selected from amino, $C_1$-$C_8$alkylamino, $C_1$-$C_8$dialkylamino, arylamino, ar$C_1$-$C_8$alkylamino, $C_3$-$C_8$cycloalkylamino, heteroalkyl$C_1$-$C_8$alkylamino, heteroalkyl$C_1$-$C_8$alkyl-N-methylamino, $C_1$-$C_8$dialkylamino ($C_1$-$C_8$)alkylamino, —N($C_1$-$C_8$alkyl)-$C_1$-$C_8$alkyl-N($C_1$-$C_8$alkyl)$_2$, —N($C_1$-$C_8$alkyl)($C_1$-$C_8$alkenyl), —N($C_1$-$C_8$alkyl)($C_3$-$C_8$cycloalkyl), heteroalkyl or substituted heteroalkyl wherein the substituent on the heteroalkyl is selected from oxo, amino, $C_1$-$C_8$alkoxy($C_1$-$C_8$)alkyl, $C_1$-$C_8$alkylamino or $C_1$-$C_8$dialkylamino;

Preferably, $R_5$ is selected from amino, $C_1$-$C_6$alkylamino, $C_1$-$C_6$ dialkylamino, $C_3$-$C_8$cycloalkylamino, arylamino, ar$C_1$-$C_6$alkylamino, heteroalkyl$C_1$-$C_6$alkylamino, —N($C_1$-$C_6$alkyl)-$C_1$-$C_6$alkyl-N($C_1$-$C_6$alkyl)$_2$, heteroalkyl or substituted heteroalkyl wherein the substituent on the heteroalkyl is selected from oxo, amino, $C_1$-$C_6$alkoxy$C_1$-$C_6$ alkyl, $C_1$-$C_6$alkylamino or $C_1$-$C_6$ dialkylamino;

m is an integer selected from 0, 1, 2 or 3;

n is an integer selected from 1 or 2;

p is an integer selected from 0 or 1; preferably, p is 0;

preferably, the point of attachment of —N($R_3$)-$A_1$-$A_2$-($A_3$)$_p$-$R_1$($R_2$) is the 5 or 6 position of the core heterocyclic ring; more preferably, the point of attachment is the 6 position; and enantiomers, diastereomers, tautomers, solvates, and pharmaceutically acceptable salts thereof.

Still another preferred embodiment of the present invention is directed to structurally novel compounds represented by the following general formula (IV):

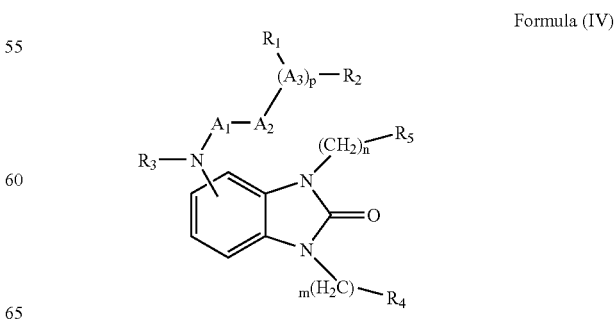

Formula (IV)

wherein

A$_1$, A$_2$ and A$_3$ are each independently a D- or L-amino acid selected from the group consisting of alanine, β-alanine, arginine, homoarginine, cyclohexylalanine, citrulline, cysteine (optionally substituted with C$_1$-C$_4$alkyl, aryl, or arC$_1$-C$_4$alkyl), 2,4-diaminobutyric acid (optionally substituted with acyl, C$_1$-C$_4$alkyl, aroyl, amidino, or MeC(NH)—), 2,3 diaminopropionic acid (optionally substituted with acyl, C$_1$-C$_4$alkyl, aroyl, amidino, or MeC(NH)—), glutamine, glycine, indanylglycine, lysine (optionally substituted with acyl, C$_1$-C$_4$alkyl, aroyl, MeC(NH)—), valine, methionine, proline, serine (optionally substituted with C$_1$-C$_4$alkyl, aryl, or arC$_1$-C$_4$alkyl), homoserine (optionally substituted with C$_1$-C$_4$alkyl, aryl, or arC$_1$-C$_4$alkyl), tetrahydroisoquinoline-3-COOH, threonine (optionally substituted with C$_1$-C$_4$alkyl, aryl, or arC$_1$-C$_4$alkyl), ornithine (optionally substituted with acyl, C$_1$-C$_4$alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, C$_1$-C$_4$alkyl, C$_1$-C$_4$alkoxy, hydroxy, C$_1$-C$_4$alkoxycarbonyl, amino, amidino, guanidino, fluorinated C$_1$-C$_4$alkyl, fluorinated C$_1$-C$_4$alkoxy, C$_1$-C$_4$alkylsulfonyl, C$_1$-C$_4$alkylcarbonyl, cyano, aryl, heteroaryl, arC$_1$-C$_4$alkyl, C$_2$-C$_4$ alkenyl, alkynyl, or nitro;

R$_1$ and R$_2$ are each independently selected from hydrogen, C$_1$-C$_8$alkyl, ar(C$_1$-C$_8$)alkyl, C$_1$-C$_8$alkoxycarbonyl, aryloxycarbonyl, ar(C$_1$-C$_8$)alkoxycarbonyl, C$_1$-C$_8$alkylcarbonyl, arylcarbonyl, ar(C$_1$-C$_8$)alkylcarbonyl, aminocarbonyl, C$_1$-C$_8$alkylaminocarbonyl, C$_1$-C$_8$dialkylaminocarbonyl, arylaminocarbonyl, diarylaminocarbonyl, ar(C$_1$-C$_8$)alkylaminocarbonyl, diar(C$_1$-C$_8$)alkylaminocarbonyl, heterocyclylcarbonyl, heteroaryl(C$_1$-C$_8$)alkyl, heteroaryloxycarbonyl, heteroaryl(C$_1$-C$_8$)alkoxycarbonyl, heteroarylcarbonyl, heteroaryl(C$_1$-C$_8$)alkylcarbonyl, heteroarylaminocarbonyl, diheteroarylaminocarbonyl, heteroaryl(C$_1$-C$_8$)alkylaminocarbonyl, and diheteroaryl(C$_1$-C$_8$)alkylaminocarbonyl, wherein said aryl, ar(C$_1$-C$_8$)alkyl, heteroaryl and heteroaryl (C$_1$-C$_8$)alkyl are optionally substituted with one or more of halogen, C$_1$-C$_8$alkyl, C$_1$-C$_8$alkoxy hydroxy, cyano, amino, and nitro; R$_1$ and R$_2$ are covalently bonded to the N-terminus of A$_3$ when p is 1 or A$_2$ when p is 0;

Preferably, R$_1$ is hydrogen;

Preferably, R$_2$ is selected from hydrogen, C$_1$-C$_8$alkyl, aryloxycarbonyl, ar(C$_1$-C$_8$)alkoxycarbonyl, C$_1$-C$_8$alkoxycarbonyl, C$_1$-C$_8$alkylcarbonyl, ar(C$_1$-C$_8$)alkylcarbonyl, arylaminocarbonyl, diarylaminocarbonyl, C$_1$-C$_8$alkylaminocarbonyl, C$_1$-C$_8$dialkylaminocarbonyl, ar(C$_1$-C$_8$alkoxy)carbonyl, and heterocyclylcarbonyl;

R$_3$ is selected from hydrogen or C$_1$-C$_8$alkyl; preferably, R$_3$ is hydrogen;

R$_4$ is selected from unsubstituted or substituted aryl, arC$_1$-C$_8$alkyl, C$_3$-C$_8$cycloalkyl, heteroaryl, or heteroaryl(C$_1$-C$_8$) alkyl, where the substituents on the aryl, arC$_1$-C$_8$alkyl, cycloalkyl, heteroaryl or heteroaryl(C$_1$-C$_8$)alkyl, group are independently selected from one or more of halogen, nitro, amino, cyano, hydroxyalkyl, C$_1$-C$_8$alkyl, C$_1$-C$_8$alkoxy, hydroxy, C$_1$-C$_4$alkylcarbonyl, C$_1$-C$_8$alkoxycarbonyl, fluorinated C$_1$-C$_4$alkyl, fluorinated C$_1$-C$_4$alkoxy or C$_1$-C$_4$alkylsulfonyl;

Preferably, R$_4$ is selected from unsubstituted or substituted aryl, arC$_1$-C$_6$alkyl, C$_3$-C$_6$cycloalkyl or heteroaryl, where the substituents on the aryl, aralkyl, cycloalkyl or heteroaryl group are independently selected from one to three substituents selected from halogen, cyano, C$_1$-C$_4$alkyl, C$_1$-C$_4$alkoxy, C$_1$-C$_4$ alkoxycarbonyl, fluorinated C$_1$-C$_4$alkyl, fluorinated C$_1$-C$_4$alkoxy or C$_1$-C$_4$alkylsulfonyl;

R$_5$ is selected from amino, C$_1$-C$_8$alkylamino, C$_1$-C$_8$dialkylamino, arylamino, arC$_1$-C$_8$alkylamino, C$_3$-C$_8$cycloalkylamino, heteroalkylC$_1$-C$_8$alkylamino, heteroalkylC$_1$-C$_8$alkyl-N-methylamino, C$_1$-C$_8$dialkylamino (C$_1$-C$_8$)alkylamino, —N(C$_1$-C$_8$alkyl)-C$_1$-C$_8$alkyl-N(C$_1$-C$_8$alkyl)$_2$, —N(C$_1$-C$_8$alkyl)(C$_1$-C$_8$alkenyl), —N(C$_1$-C$_8$alkyl)(C$_3$-C$_8$cycloalkyl), heteroalkyl or substituted heteroalkyl wherein the substituent on the heteroalkyl is selected from oxo, amino, C$_1$-C$_8$alkoxy(C$_1$-C$_8$)alkyl, C$_1$-C$_8$alkylamino or C$_1$-C$_8$dialkylamino;

Preferably, R$_5$ is selected from amino, C$_1$-C$_6$alkylamino, C$_1$-C$_6$ dialkylamino, C$_3$-C$_8$cycloalkylamino, arylamino, arC$_1$-C$_6$alkylamino, heteroalkylC$_1$-C$_6$alkylamino, —N(C$_1$-C$_6$alkyl)-C$_1$-C$_6$alkyl-N(C$_1$-C$_6$alkyl)$_2$, heteroalkyl or substituted heteroalkyl wherein the substituent on the heteroalkyl is selected from oxo, amino, C$_1$-C$_6$alkoxyC$_1$-C$_6$ alkyl, C$_1$-C$_6$alkylamino or C$_1$-C$_6$ dialkylamino;

m is an integer selected from 0, 1, 2 or 3;

n is an integer selected from 1 or 2;

p is an integer selected from 0 or 1; preferably, p is 0;

preferably, the point of attachment of —N(R$_3$)-A$_1$-A$_2$-(A$_3$)$_p$-R$_1$(R$_2$) is the 5 or 6 position of the core heterocyclic ring; more preferably, the point of attachment is the 6 position; and enantiomers, diastereomers, tautomers, solvates, and pharmaceutically acceptable salts thereof.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

An example of the invention is a method of treating a disorder (preferably, a platelet-mediated thrombotic disorder) selected from arterial and/or venous thrombosis, acute myocardial infarction, reocclusion following thrombolytic therapy and/or angioplasty, inflammation, unstable angina, stroke, restenosis, atherosclerosis, ischemic conditions, hypertension, heart failure, arrhythmia, glomerulonephritis, osteoporosis, angiogenesis and related disorders, cancer, neurodegenerative disorders and a variety of vaso-occlusive disorders in a subject in need thereof comprising administering to the subject a therapeutically effective amount of any of the compounds or pharmaceutical compositions described above. In a preferred embodiment, the therapeutically effective amount of the compound is from about 0.1 mg/kg/day to about 300 mg/kg/day.

Also included in the invention is the use of any of the compounds described above for the preparation of a medicament for a disorder (preferably, a platelet-mediated thrombotic disorder) selected from arterial and/or venous thrombosis, acute myocardial infarction, reocclusion following thrombolytic therapy and/or angioplasty, inflammation, unstable angina, stroke, restenosis, atherosclerosis, ischemic conditions, hypertension, heart failure, arrhythmia, glomerulonephritis, osteoporosis, angiogenesis and related disorders, cancer, neurodegenerative disorders or a variety of vaso-occlusive disorders in a subject in need thereof.

DETAILED DESCRIPTION OF THE INVENTION

The present invention is directed to structurally novel compounds represented by the following general formula (I):

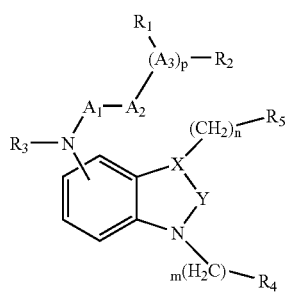

Formula (I)

wherein $A_1$, $A_2$ and $A_3$ are each independently a D- or L-amino acid selected from the group consisting of alanine, β-alanine, arginine, homoarginine, cyclohexylalanine, citrulline, cysteine (optionally substituted with $C_1$-$C_4$alkyl, aryl, or ar$C_1$-$C_4$alkyl), 2,4-diaminobutyric acid (optionally substituted with acyl, $C_1$-$C_4$alkyl, aroyl, amidino, or MeC(NH)—), 2,3 diaminopropionic acid (optionally substituted with acyl, $C_1$-$C_4$alkyl, aroyl, amidino, or MeC(NH)—), glutamine, glycine, indanylglycine, lysine (optionally substituted with acyl, $C_1$-$C_4$alkyl, aroyl, MeC(NH)—), valine, methionine, proline, serine (optionally substituted with $C_1$-$C_4$alkyl, aryl, or ar$C_1$-$C_4$alkyl), homoserine (optionally substituted with $C_1$-$C_4$alkyl, aryl, or ar$C_1$-$C_4$alkyl), tetrahydroisoquinoline-3-COOH, threonine (optionally substituted with $C_1$-$C_4$alkyl, aryl, or ar$C_1$-$C_4$alkyl), ornithine (optionally substituted with acyl, $C_1$-$C_4$alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

$R_1$ and $R_2$ are each independently selected from hydrogen, $C_1$-$C_8$alkyl, ar($C_1$-$C_8$)alkyl, $C_1$-$C_8$alkoxycarbonyl, aryloxycarbonyl, ar($C_1$-$C_8$)alkoxycarbonyl, $C_1$-$C_8$alkylcarbonyl, arylcarbonyl, ar($C_1$-$C_8$)alkylcarbonyl, aminocarbonyl, $C_1$-$C_8$alkylaminocarbonyl, $C_1$-$C_8$dialkylaminocarbonyl, arylaminocarbonyl, diarylaminocarbonyl, ar($C_1$-$C_8$)alkylaminocarbonyl, diar($C_1$-$C_8$)alkylaminocarbonyl, heterocyclylcarbonyl, heteroaryl($C_1$-$C_8$)alkyl, heteroaryloxycarbonyl, heteroaryl($C_1$-$C_8$)alkoxycarbonyl, heteroarylcarbonyl, heteroaryl($C_1$-$C_8$)alkylcarbonyl, heteroarylaminocarbonyl, diheteroarylaminocarbonyl, heteroaryl($C_1$-$C_8$)alkylaminocarbonyl, and diheteroaryl($C_1$-$C_8$)alkylaminocarbonyl, wherein said aryl, ar($C_1$-$C_8$)alkyl, heteroaryl and heteroaryl($C_1$-$C_8$)alkyl are optionally substituted with one or more of halogen, $C_1$-$C_8$alkyl, $C_1$-$C_8$alkoxy hydroxy, cyano, amino, and nitro; $R_1$ and $R_2$ are covalently bonded to the N-terminus of $A_3$ when p is 1 or $A_2$ when p is 0;

Preferably $R_1$ is hydrogen;

Preferably, $R_2$ is selected from hydrogen, $C_1$-$C_8$alkyl, aryloxycarbonyl, ar($C_1$-$C_8$)alkoxycarbonyl, $C_1$-$C_8$alkoxycarbonyl, $C_1$-$C_8$alkylcarbonyl, ar($C_1$-$C_8$)alkylcarbonyl, arylaminocarbonyl, diarylaminocarbonyl, $C_1$-$C_8$alkylaminocarbonyl, $C_1$-$C_8$dialkylaminocarbonyl, ar($C_1$-$C_8$alkoxy)carbonyl, and heterocyclylcarbonyl;

$R_3$ is selected from hydrogen or $C_1$-$C_8$ alkyl; preferably, $R_3$ is hydrogen;

$R_4$ is selected from unsubstituted or substituted aryl, ar$C_1$-$C_8$alkyl, $C_3$-$C_8$cycloalkyl, heteroaryl, or heteroaryl($C_1$-$C_8$)alkyl, where the substituents on the aryl, ar$C_1$-$C_8$alkyl, cycloalkyl, heteroaryl or heteroaryl($C_1$-$C_8$)alkyl, group are independently selected from one or more of halogen, nitro, amino, cyano, hydroxyalkyl, $C_1$-$C_8$alkyl, $C_1$-$C_8$alkoxy, hydroxy, $C_1$-$C_4$alkylcarbonyl, $C_1$-$C_8$alkoxycarbonyl, fluorinated $C_1$-$C_4$alkyl, fluorinated $C_1$-$C_4$alkoxy or $C_1$-$C_4$alkylsulfonyl;

Preferably, $R_4$ is selected from unsubstituted or substituted aryl, ar$C_1$-$C_6$alkyl, $C_3$-$C_6$cycloalkyl or heteroaryl, where the substituents on the aryl, aralkyl, cycloalkyl or heteroaryl group are independently selected from one to three substituents selected from halogen, cyano, $C_1$-$C_4$alkyl, $C_1$-$C_4$alkoxy, $C_1$-$C_4$ alkoxycarbonyl, fluorinated $C_1$-$C_4$alkyl, fluorinated $C_1$-$C_4$alkoxy or $C_1$-$C_4$alkylsulfonyl;

$R_5$ is selected from amino, $C_1$-$C_8$alkylamino, $C_1$-$C_8$dialkylamino, arylamino, ar$C_1$-$C_8$alkylamino, $C_3$-$C_8$cycloalkylamino, heteroalkyl$C_1$-$C_8$alkylamino, heteroalkyl$C_1$-$C_8$alkyl-N-methylamino, $C_1$-$C_8$dialkylamino ($C_1$-$C_8$)alkylamino, —N($C_1$-$C_8$alkyl)-$C_1$-$C_8$alkyl-N($C_1$-$C_8$alkyl)$_2$, —N($C_1$-$C_8$alkyl)($C_1$-$C_8$alkenyl), —N($C_1$-$C_8$alkyl)($C_3$-$C_8$cycloalkyl), heteroalkyl or substituted heteroalkyl wherein the substituent on the heteroalkyl is selected from oxo, amino, $C_1$-$C_8$alkoxy($C_1$-$C_8$)alkyl, $C_1$-$C_8$alkylamino or $C_1$-$C_8$dialkylamino;

Preferably, $R_5$ is selected from amino, $C_1$-$C_6$alkylamino, $C_1$-$C_6$ dialkylamino, $C_3$-$C_8$cycloalkylamino, arylamino, ar$C_1$-$C_6$alkylamino, heteroalkyl$C_1$-$C_6$alkylamino, —N($C_1$-$C_6$alkyl)-$C_1$-$C_6$alkyl-N($C_1$-$C_6$alkyl)$_2$, heteroalkyl or substituted heteroalkyl wherein the substituent on the heteroalkyl is selected from oxo, amino, $C_1$-$C_6$alkoxy$C_1$-$C_6$ alkyl, $C_1$-$C_6$alkylamino or $C_1$-$C_6$ dialkylamino;

X is N or C;

Y is N, C or —CO—;

Provided that when Y is N, then X is C and there is a double bond between X and Y; Provided also that when Y is C, then X is C and there is a double bond between X and Y; And provided also that when Y is —CO—, then X is N and there is a single bond between X and Y;

m is an integer selected from 0, 1, 2 or 3;

n is an integer selected from 1 or 2;

p is an integer selected from 0 or 1; preferably, p is 0;

preferably, the point of attachment of —N($R_3$)-$A_1$-$A_2$-($A_3$)$_p$-$R_1$($R_2$) is the 5 or 6 position of the core heterocyclic ring; more preferably, the point of attachment is the 6 position; and enantiomers, diastereomers, tautomers, solvates, and pharmaceutically acceptable salts thereof.

Preferred compounds of formula (I) are those wherein (1) $A_1$ is an unsubstituted or substituted amino acid residue selected from the group consisting of phenylalanine, cyclohexylalanine, alanine, β-alanine, heteroarylalanine, naphthylalanine, homophenylalanine, arylglycine, heteroarylglycine, aryl-β-alanine, and heteroaryl-β-alanine wherein the substituents on the amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

(2) more preferably, $A_1$ is an unsubstituted or substituted amino acid residue selected from the group consisting of phenylalanine, cyclohexylalanine, and heteroarylalanine, wherein the substituents on the amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

(3) even more preferably, $A_1$ is an unsubstituted amino acid residue selected from the group consisting of phenylalanine, cyclohexylalanine, and heteroarylalanine;

(4) most preferably, $A_1$ is phenylalanine or cyclohexylalanine;

(5) $A_2$ is an amino acid selected from the group consisting of arginine, homoarginine, 2,4-diaminobutyric acid (optionally substituted with acyl, $C_1$-$C_4$alkyl, aroyl, amidino, or MeC(NH)—), 2,3 diaminopropionic acid (optionally substituted with acyl, $C_1$-$C_4$alkyl, aroyl, amidino, or MeC(NH)—), glutamine, and lysine (optionally substituted with acyl, $C_1$-$C_4$alkyl, aroyl, amidino or MeC(NH)—);

(6) preferably, $A_2$ is an amino acid selected from the group consisting of arginine, homoarginine, 2,4-diaminobutyric acid, 2,3-diaminopropionic acid, glutamine, and lysine;

(7) more preferably, $A_2$ is arginine;

(8) $R_1$ is hydrogen;

(9) $R_2$ is selected from hydrogen, $C_1$-$C_8$alkyl, aryloxycarbonyl, $C_1$-$C_8$alkoxycarbonyl, $C_1$-$C_8$alkylcarbonyl, arylaminocarbonyl, diarylaminocarbonyl, $C_1$-$C_8$alkylaminocarbonyl, $C_1$-$C_8$dialkylaminocarbonyl, ar($C_1$-$C_8$alkoxy)carbonyl, and heterocyclylcarbonyl, wherein said aryl, ar($C_1$-$C_8$) alkyl, heteroaryl and heteroaryl($C_1$-$C_8$)alkyl are optionally substituted with one or more of halogen, $C_1$-$C_8$alkyl, and $C_1$-$C_8$alkoxy;

(10) more preferably, $R_2$ is selected from $C_1$-$C_8$alkylcarbonyl, aryloxycarbonyl, arylaminocarbonyl, and ar($C_1$-$C_8$alkoxy)carbonyl, wherein said aryl, ar($C_1$-$C_8$)alkyl, heteroaryl and heteroaryl($C_1$-$C_8$) alkyl are optionally substituted with one or more of halogen, $C_1$-$C_8$alkyl, and $C_1$-$C_8$alkoxy;

(11) most preferably, $R_2$ is selected from acetyl, Fmoc, and p-methoxyphenylaminocarbonyl;

(12) $R_3$ is hydrogen;

(13) $R_4$ is substituted aryl, where the substituents on the aryl are independently selected from one to three substituents selected from halogen, cyano, $C_1$-$C_4$alkyl, $C_1$-$C_4$alkoxy, $C_1$-$C_4$ alkoxycarbonyl, fluorinated $C_1$-$C_4$alkyl, fluorinated $C_1$-$C_4$alkoxy or $C_1$-$C_4$alkylsulfonyl;

(14) more preferably, $R_4$ is substituted aryl, where the substituents on the aryl are one to three halogen substituents;

(15) most preferably, $R_4$ is 4-fluorophenyl;

(16) $R_5$ is selected from amino, $C_1$-$C_6$alkylamino, $C_1$-$C_6$ dialkylamino, $C_3$-$C_8$cycloalkylamino, arylamino, ar$C_1$-$C_6$alkylamino, heteroalkyl$C_1$-$C_6$alkylamino, —N($C_1$-$C_6$alkyl)-$C_1$-$C_6$alkyl-N($C_1$-$C_6$alkyl)$_2$, heteroalkyl or substituted heteroalkyl wherein the substituent on the heteroalkyl is selected from oxo, amino, $C_1$-$C_6$alkoxy$C_1$-$C_6$ alkyl, $C_1$-$C_6$alkylamino or $C_1$-$C_6$ dialkylamino;

(17) preferably, $R_5$ is $C_1$-$C_6$alkylamino or $C_3$-$C_8$cycloalkylamino;

(18) m is one;

(19) n is one;

(20) p is 0; and combinations of (1) through (20) above.

A preferred embodiment of the present invention is directed to structurally novel compounds represented by the following general formula (II):

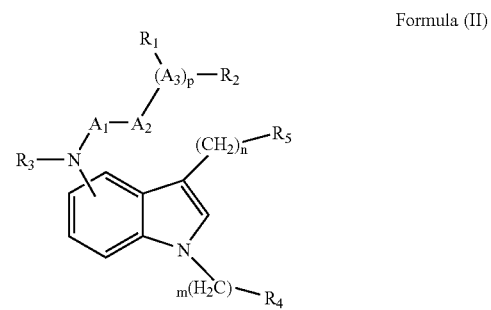

Formula (II)

wherein $A_1$, $A_2$ and $A_3$ are each independently a D- or L-amino acid selected from the group consisting of alanine, β-alanine, arginine, homoarginine, cyclohexylalanine, citrulline, cysteine (optionally substituted with $C_1$-$C_4$alkyl, aryl, or ar$C_1$-$C_4$alkyl), 2,4-diaminobutyric acid (optionally substituted with acyl, $C_1$-$C_4$alkyl, aroyl, amidino, or MeC(NH)—), 2,3 diaminopropionic acid (optionally substituted with acyl, $C_1$-$C_4$alkyl, aroyl, amidino, or MeC(NH)—), glutamine, glycine, indanylglycine, lysine (optionally substituted with acyl, $C_1$-$C_4$alkyl, aroyl, MeC(NH)—), valine, methionine, proline, serine (optionally substituted with $C_1$-$C_4$alkyl, aryl, or ar$C_1$-$C_4$alkyl), homoserine (optionally substituted with $C_1$-$C_4$alkyl, aryl, or ar$C_1$-$C_4$alkyl), tetrahydroisoquinoline-3-COOH, threonine (optionally substituted with $C_1$-$C_4$alkyl, aryl, or ar$C_1$-$C_4$alkyl), ornithine (optionally substituted with acyl, $C_1$-$C_4$alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

$R_1$ and $R_2$ are each independently selected from hydrogen, $C_1$-$C_8$alkyl, ar($C_1$-$C_8$)alkyl, $C_1$-$C_8$alkoxycarbonyl, aryloxycarbonyl, ar($C_1$-$C_8$)alkoxycarbonyl, $C_1$-$C_8$alkylcarbonyl, arylcarbonyl, ar($C_1$-$C_8$)alkylcarbonyl, aminocarbonyl, $C_1$-$C_8$alkylaminocarbonyl, $C_1$-$C_8$dialkylaminocarbonyl, arylaminocarbonyl, diarylaminocarbonyl, ar($C_1$-$C_8$)alkylaminocarbonyl, diar($C_1$-$C_8$)alkylaminocarbonyl, heterocyclylcarbonyl, heteroaryl($C_1$-$C_8$)alkyl, heteroaryloxycarbonyl, heteroaryl($C_1$-$C_8$)alkoxycarbonyl, heteroarylcarbonyl, heteroaryl($C_1$-$C_8$)alkylcarbonyl, heteroarylaminocarbonyl, diheteroarylaminocarbonyl, heteroaryl($C_1$-$C_8$)alkylaminocarbonyl, and diheteroaryl($C_1$-$C_8$)alkylaminocarbonyl, wherein said aryl, ar($C_1$-$C_8$)alkyl, heteroaryl and heteroaryl ($C_1$-$C_8$)alkyl are optionally substituted with one or more of halogen, $C_1$-$C_8$alkyl, $C_1$-$C_8$alkoxy hydroxy, cyano, amino, and nitro; $R_1$ and $R_2$ are covalently bonded to the N-terminus of $A_3$ when p is 1 or $A_2$ when p is 0;

Preferably $R_1$ is hydrogen;

Preferably, $R_2$ is selected from hydrogen, $C_1$-$C_8$alkyl, aryloxycarbonyl, ar($C_1$-$C_8$)alkoxycarbonyl, $C_1$-$C_8$alkoxycarbonyl, $C_1$-$C_8$alkylcarbonyl, ar($C_1$-$C_8$)alkylcarbonyl, arylaminocarbonyl, diarylaminocarbonyl, $C_1$-$C_8$alkylaminocarbonyl, $C_1$-$C_8$dialkylaminocarbonyl, ar($C_1$-$C_8$alkoxy)carbonyl, and heterocyclylcarbonyl, wherein said aryl, ar($C_1$-$C_8$)alkyl, heteroaryl and heteroaryl ($C_1$-$C_8$)alkyl are optionally substituted with one or more of halogen, $C_1$-$C_8$alkyl, and $C_1$-$C_8$alkoxy;

$R_3$ is selected from hydrogen or $C_1$-$C_8$ alkyl; preferably, $R_3$ is hydrogen;

$R_4$ is selected from unsubstituted or substituted aryl, ar$C_1$-$C_8$alkyl, $C_3$-$C_8$cycloalkyl, heteroaryl, or heteroaryl($C_1$-$C_8$) alkyl, where the substituents on the aryl, ar$C_1$-$C_8$alkyl, cycloalkyl, heteroaryl or heteroaryl($C_1$-$C_8$)alkyl, group are independently selected from one or more of halogen, nitro, amino, cyano, hydroxyalkyl, $C_1$-$C_8$alkyl, $C_1$-$C_8$alkoxy, hydroxy, $C_1$-$C_4$alkylcarbonyl, $C_1$-$C_8$alkoxycarbonyl, fluorinated $C_1$-$C_4$alkyl, fluorinated $C_1$-$C_4$alkoxy or $C_1$-$C_4$alkylsulfonyl;

Preferably, $R_4$ is selected from unsubstituted or substituted aryl, ar$C_1$-$C_6$alkyl, $C_3$-$C_6$cycloalkyl or heteroaryl, where the substituents on the aryl, aralkyl, cycloalkyl or heteroaryl group are independently selected from one to three substituents selected from halogen, cyano, $C_1$-$C_4$alkyl, $C_1$-$C_4$alkoxy, $C_1$-$C_4$ alkoxycarbonyl, fluorinated $C_1$-$C_4$alkyl, fluorinated $C_1$-$C_4$alkoxy or $C_1$-$C_4$alkylsulfonyl;

$R_5$ is selected from amino, $C_1$-$C_8$alkylamino, $C_1$-$C_8$dialkylamino, arylamino, ar$C_1$-$C_8$alkylamino, $C_3$-$C_8$cycloalkylamino, heteroalkyl$C_1$-$C_8$alkylamino, heteroalkyl$C_1$-$C_8$alkyl-N-methylamino, $C_1$-$C_8$dialkylamino ($C_1$-$C_8$)alkylamino, —N($C_1$-$C_8$alkyl)-$C_1$-$C_8$alkyl-N($C_1$-$C_8$alkyl)$_2$, —N($C_1$-$C_8$alkyl)($C_1$-$C_8$alkenyl), —N($C_1$-$C_8$alkyl)($C_3$-$C_8$cycloalkyl), heteroalkyl or substituted heteroalkyl wherein the substituent on the heteroalkyl is selected from oxo, amino, $C_1$-$C_8$alkoxy($C_1$-$C_8$)alkyl, $C_1$-$C_8$alkylamino or $C_1$-$C_8$dialkylamino;

Preferably, $R_5$ is selected from amino, $C_1$-$C_6$alkylamino, $C_1$-$C_6$dialkylamino, $C_3$-$C_8$cycloalkylamino, arylamino, ar$C_1$-$C_6$alkylamino, heteroalkyl$C_1$-$C_6$alkylamino, —N($C_1$-$C_6$alkyl)-$C_1$-$C_6$alkyl-N($C_1$-$C_6$alkyl)$_2$, heteroalkyl or substituted heteroalkyl wherein the substituent on the heteroalkyl is selected from oxo, amino, $C_1$-$C_6$alkoxy$C_1$-$C_6$ alkyl, $C_1$-$C_6$alkylamino or $C_1$-$C_6$dialkylamino;

m is an integer selected from 0, 1, 2 or 3;

n is an integer selected from 1 or 2;

preferably, the point of attachment of —N($R_3$)-$A_1$-$A_2$-($A_3$)$_p$-$R_1$($R_2$) is the 5 or 6 position of the core heterocyclic ring; more preferably, the point of attachment is the 6 position; and enantiomers, diastereomers, tautomers, solvates, and pharmaceutically acceptable salts thereof.

Preferred compounds of formula (II) are those wherein (1) $A_1$ is an unsubstituted or substituted amino acid residue selected from the group consisting of phenylalanine, cyclohexylalanine, alanine, β-alanine, heteroarylalanine, naphthylalanine, homophenylalanine, arylglycine, heteroarylglycine, aryl-β-alanine, and heteroaryl-β-alanine wherein the substituents on the amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

(2) more preferably, $A_1$ is an unsubstituted or substituted amino acid residue selected from the group consisting of phenylalanine, cyclohexylalanine, and heteroarylalanine, wherein the substituents on the amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

(3) even more preferably, $A_1$ is an unsubstituted amino acid residue selected from the group consisting of phenylalanine, cyclohexylalanine, and heteroarylalanine;

(4) most preferably, $A_1$ is phenylalanine or cyclohexylalanine;

(5) $A_2$ is an amino acid selected from the group consisting of arginine, homoarginine, 2,4-diaminobutyric acid (optionally substituted with acyl, $C_1$-$C_4$alkyl, aroyl, amidino, or MeC(NH)—), 2,3 diaminopropionic acid (optionally substituted with acyl, $C_1$-$C_4$alkyl, aroyl, amidino, or MeC(NH)—), glutamine, and lysine (optionally substituted with acyl, $C_1$-$C_4$alkyl, aroyl, amidino or MeC(NH)—);

(6) preferably, $A_2$ is an amino acid selected from the group consisting of arginine, homoarginine, 2,4-diaminobutyric acid, 2,3-diaminopropionic acid, glutamine, and lysine;

(7) more preferably, $A_2$ is arginine;

(8) $R_1$ is hydrogen;

(9) $R_2$ is selected from hydrogen, $C_1$-$C_8$alkyl, aryloxycarbonyl, $C_1$-$C_8$alkoxycarbonyl, $C_1$-$C_8$alkylcarbonyl, arylaminocarbonyl, diarylaminocarbonyl, $C_1$-$C_8$alkylaminocarbonyl, $C_1$-$C_8$dialkylaminocarbonyl, ar($C_1$-$C_8$alkoxy)carbonyl, and heterocyclylcarbonyl, wherein said aryl, ar($C_1$-$C_8$)alkyl, heteroaryl and heteroaryl($C_1$-$C_8$)alkyl are optionally substituted with one or more of halogen, $C_1$-$C_8$alkyl, and $C_1$-$C_8$alkoxy;

(10) more preferably, $R_2$ is selected from $C_1$-$C_8$alkylcarbonyl, aryloxycarbonyl, arylaminocarbonyl, and ar($C_1$-$C_8$alkoxy)carbonyl, wherein said aryl, ar($C_1$-$C_8$)alkyl, heteroaryl and heteroaryl($C_1$-$C_8$) alkyl are optionally substituted with one or more of halogen, $C_1$-$C_8$alkyl, and $C_1$-$C_8$alkoxy;

(11) most preferably, $R_2$ is selected from acetyl, Fmoc, and p-methoxyphenylaminocarbonyl;

(12) $R_3$ is hydrogen;

(13) $R_4$ is substituted aryl, where the substituents on the aryl are independently selected from one to three substituents selected from halogen, cyano, $C_1$-$C_4$alkyl, $C_1$-$C_4$alkoxy, $C_1$-$C_4$ alkoxycarbonyl, fluorinated $C_1$-$C_4$alkyl, fluorinated $C_1$-$C_4$alkoxy or $C_1$-$C_4$alkylsulfonyl;

(14) more preferably, $R_4$ is substituted aryl, where the substituents on the aryl are one to three halogen substituents;

(15) most preferably, $R_4$ is 4-fluorophenyl;

(16) $R_5$ is selected from amino, $C_1$-$C_6$alkylamino, $C_1$-$C_6$ dialkylamino, $C_3$-$C_8$cycloalkylamino, arylamino, ar$C_1$-$C_6$alkylamino, heteroalkyl$C_1$-$C_6$alkylamino, —N($C_1$-

$C_6$alkyl)-$C_1$-$C_6$alkyl-N($C_1$-$C_6$alkyl)$_2$, heteroalkyl or substituted heteroalkyl wherein the substituent on the heteroalkyl is selected from oxo, amino, $C_1$-$C_6$alkoxy$C_1$-$C_6$ alkyl, $C_1$-$C_6$alkylamino or $C_1$-$C_6$ dialkylamino;

(17) preferably, $R_5$ is $C_1$-$C_6$alkylamino or $C_3$-$C_8$cycloalkylamino;

(18) m is one;

(19) n is one;

(20) p is 0; and combinations of (1) through (20) above.

p is an integer selected from 0 or 1; preferably, p is 0; and enantiomers, diastereomers, tautomers, solvates, and pharmaceutically acceptable salts thereof.

Another preferred embodiment of the present invention is directed to structurally novel compounds represented by the following general formula (III):

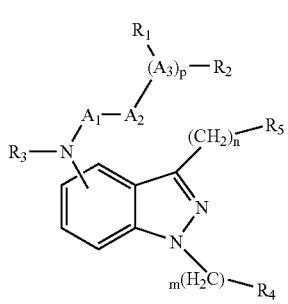

Formula (III)

wherein $A_1$, $A_2$ and $A_3$ are each independently a D- or L-amino acid selected from the group consisting of alanine, β-alanine, arginine, homoarginine, cyclohexylalanine, citrulline, cysteine (optionally substituted with $C_1$-$C_4$alkyl, aryl, or ar$C_1$-$C_4$alkyl), 2,4-diaminobutyric acid (optionally substituted with acyl, $C_1$-$C_4$alkyl, aroyl, amidino, or MeC(NH)—), 2,3 diaminopropionic acid (optionally substituted with acyl, $C_1$-$C_4$alkyl, aroyl, amidino, or MeC(NH)—), glutamine, glycine, indanylglycine, lysine (optionally substituted with acyl, $C_1$-$C_4$alkyl, aroyl, MeC(NH)—), valine, methionine, proline, serine (optionally substituted with $C_1$-$C_4$alkyl, aryl, or ar$C_1$-$C_4$alkyl), homoserine (optionally substituted with $C_1$-$C_4$alkyl, aryl, or ar$C_1$-$C_4$alkyl), tetrahydroisoquinoline-3-COOH, threonine (optionally substituted with $C_1$-$C_4$alkyl, aryl, or ar$C_1$-$C_4$alkyl), ornithine (optionally substituted with acyl, $C_1$-$C_4$alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

$R_1$ and $R_2$ are each independently selected from hydrogen, $C_1$-$C_8$alkyl, ar($C_1$-$C_8$)alkyl, $C_1$-$C_8$alkoxycarbonyl, aryloxycarbonyl, ar($C_1$-$C_8$)alkoxycarbonyl, $C_1$-$C_8$alkylcarbonyl, arylcarbonyl, ar($C_1$-$C_8$)alkylcarbonyl, aminocarbonyl, $C_1$-$C_8$alkylaminocarbonyl, $C_1$-$C_8$dialkylaminocarbonyl, arylaminocarbonyl, diarylaminocarbonyl, ar($C_1$-$C_8$)alkylaminocarbonyl, diar($C_1$-$C_8$)alkylaminocarbonyl, heterocyclylcarbonyl, heteroaryl($C_1$-$C_8$)alkyl, heteroaryloxycarbonyl, heteroaryl($C_1$-$C_8$)alkoxycarbonyl, heteroarylcarbonyl, heteroaryl($C_1$-$C_8$)alkylcarbonyl, heteroarylaminocarbonyl, diheteroarylaminocarbonyl, heteroaryl($C_1$-$C_8$)alkylaminocarbonyl, and diheteroaryl($C_1$-$C_8$)alkylaminocarbonyl, wherein said aryl, ar($C_1$-$C_8$)alkyl, heteroaryl and heteroaryl ($C_1$-$C_8$)alkyl are optionally substituted with one or more of halogen, $C_1$-$C_8$alkyl, $C_1$-$C_8$alkoxy hydroxy, cyano, amino, and nitro; R. and $R_2$ are covalently bonded to the N-terminus of $A_3$ when p is 1 or $A_2$ when p is 0;

Preferably $R_1$ is hydrogen;

Preferably, $R_2$ is selected from hydrogen, $C_1$-$C_8$alkyl, aryloxycarbonyl, ar($C_1$-$C_8$)alkoxycarbonyl, $C_1$-$C_8$alkoxycarbonyl, $C_1$-$C_8$alkylcarbonyl, ar($C_1$-$C_8$)alkylcarbonyl, arylaminocarbonyl, diarylaminocarbonyl, $C_1$-$C_8$alkylaminocarbonyl, $C_1$-$C_8$dialkylaminocarbonyl, ar($C_1$-$C_8$alkoxy)carbonyl, and heterocyclylcarbonyl, wherein said aryl, ar($C_1$-$C_8$)alkyl, heteroaryl and heteroaryl ($C_1$-$C_8$)alkyl are optionally substituted with one or more of halogen, $C_1$-$C_8$alkyl, and $C_1$-$C_8$alkoxy;

$R_3$ is selected from hydrogen or $C_1$-$C_8$ alkyl; preferably, $R_3$ is hydrogen;

$R_4$ is selected from unsubstituted or substituted aryl, ar$C_1$-$C_8$alkyl, $C_3$-$C_8$cycloalkyl, heteroaryl, or heteroaryl($C_1$-$C_8$) alkyl, where the substituents on the aryl, ar$C_1$-$C_8$alkyl, cycloalkyl, heteroaryl or heteroaryl($C_1$-$C_8$)alkyl, group are independently selected from one or more of halogen, nitro, amino, cyano, hydroxyalkyl, $C_1$-$C_8$alkyl, $C_1$-$C_8$alkoxy, hydroxy, $C_1$-$C_4$alkylcarbonyl, $C_1$-$C_8$alkoxycarbonyl, fluorinated $C_1$-$C_4$alkyl, fluorinated $C_1$-$C_4$alkoxy or $C_1$-$C_4$alkylsulfonyl;

Preferably, $R_4$ is selected from unsubstituted or substituted aryl, ar$C_1$-$C_6$alkyl, $C_3$-$C_6$cycloalkyl or heteroaryl, where the substituents on the aryl, aralkyl, cycloalkyl or heteroaryl group are independently selected from one to three substituents selected from halogen, cyano, $C_1$-$C_4$alkyl, $C_1$-$C_4$alkoxy, $C_1$-$C_4$ alkoxycarbonyl, fluorinated $C_1$-$C_4$alkyl, fluorinated $C_1$-$C_4$alkoxy or $C_1$-$C_4$alkylsulfonyl;

$R_5$ is selected from amino, $C_1$-$C_8$alkylamino, $C_1$-$C_8$dialkylamino, arylamino, ar$C_1$-$C_8$alkylamino, $C_3$-$C_8$cycloalkylamino, heteroalkyl$C_1$-$C_8$alkylamino, heteroalkyl$C_1$-$C_8$alkyl-N-methylamino, $C_1$-$C_8$dialkylamino ($C_1$-$C_8$)alkylamino, —N($C_1$-$C_8$alkyl)-$C_1$-$C_8$alkyl-N($C_1$-$C_8$alkyl)$_2$, —N($C_1$-$C_8$alkyl)($C_1$-$C_8$alkenyl), —N($C_1$-$C_8$alkyl)($C_3$-$C_8$cycloalkyl), heteroalkyl or substituted heteroalkyl wherein the substituent on the heteroalkyl is selected from oxo, amino, $C_1$-$C_8$alkoxy($C_1$-$C_8$)alkyl, $C_1$-$C_8$alkylamino or $C_1$-$C_8$dialkylamino;

Preferably, $R_5$ is selected from amino, $C_1$-$C_6$alkylamino, $C_1$-$C_6$ dialkylamino, $C_3$-$C_8$cycloalkylamino, arylamino, ar$C_1$-$C_6$alkylamino, heteroalkyl$C_1$-$C_6$alkylamino, —N($C_1$-$C_6$alkyl)-$C_1$-$C_6$alkyl-N($C_1$-$C_6$alkyl)$_2$, heteroalkyl or substituted heteroalkyl wherein the substituent on the heteroalkyl is selected from oxo, amino, $C_1$-$C_6$alkoxy$C_1$-$C_6$ alkyl, $C_1$-$C_6$alkylamino or $C_1$-$C_6$ dialkylamino;

m is an integer selected from 0, 1, 2 or 3;

n is an integer selected from 1 or 2;

p is an integer selected from 0 or 1; preferably, p is 0;

preferably, the point of attachment of —N($R_3$)-$A_1$-$A_2$-($A_3$)$_p$-$R_1$($R_2$) is the 5 or 6 position of the core heterocyclic ring; more preferably, the point of attachment is the 6 position; and enantiomers, diastereomers, tautomers, solvates, and pharmaceutically acceptable salts thereof.

Preferred compounds of formula (III) are those wherein (1) $A_1$ is an unsubstituted or substituted amino acid residue selected from the group consisting of phenylalanine, cyclohexylalanine, alanine, β-alanine, heteroarylalanine, naphthylalanine, homophenylalanine, arylglycine, heteroarylglycine, aryl-β-alanine, and heteroaryl-β-alanine wherein the substituents on the amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

(2) more preferably, $A_1$ is an unsubstituted or substituted amino acid residue selected from the group consisting of phenylalanine, cyclohexylalanine, and heteroarylalanine, wherein the substituents on the amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

(3) even more preferably, $A_1$ is an unsubstituted amino acid residue selected from the group consisting of phenylalanine, cyclohexylalanine, and heteroarylalanine;

(4) most preferably, $A_1$ is phenylalanine or cyclohexylalanine;

(5) $A_2$ is an amino acid selected from the group consisting of arginine, homoarginine, 2,4-diaminobutyric acid (optionally substituted with acyl, $C_1$-$C_4$alkyl, aroyl, amidino, or MeC(NH)—), 2,3 diaminopropionic acid (optionally substituted with acyl, $C_1$-$C_4$alkyl, aroyl, amidino, or MeC(NH)—), glutamine, and lysine (optionally substituted with acyl, $C_1$-$C_4$alkyl, aroyl, amidino or MeC(NH)—);

(6) preferably, $A_2$ is an amino acid selected from the group consisting of arginine, homoarginine, 2,4-diaminobutyric acid, 2,3-diaminopropionic acid, glutamine, and lysine;

(7) more preferably, $A_2$ is arginine;

(8) $R_1$ is hydrogen;

(9) $R_2$ is selected from hydrogen, $C_1$-$C_8$alkyl, aryloxycarbonyl, $C_1$-$C_8$alkoxycarbonyl, $C_1$-$C_8$alkylcarbonyl, arylaminocarbonyl, diarylaminocarbonyl, $C_1$-$C_8$alkylaminocarbonyl, $C_1$-$C_8$dialkylaminocarbonyl, ar($C_1$-$C_8$alkoxy)carbonyl, and heterocyclylcarbonyl, wherein said aryl, ar($C_1$-$C_8$) alkyl, heteroaryl and heteroaryl($C_1$-$C_8$)alkyl are optionally substituted with one or more of halogen, $C_1$-$C_8$alkyl, and $C_1$-$C_8$alkoxy;

(10) more preferably, $R_2$ is selected from $C_1$-$C_8$alkylcarbonyl, aryloxycarbonyl, arylaminocarbonyl, and ar($C_1$-$C_8$alkoxy)carbonyl, wherein said aryl, ar($C_1$-$C_8$)alkyl, heteroaryl and heteroaryl($C_1$-$C_8$) alkyl are optionally substituted with one or more of halogen, $C_1$-$C_8$alkyl, and $C_1$-$C_8$alkoxy;

(11) most preferably, $R_2$ is selected from acetyl, Fmoc, and p-methoxyphenylaminocarbonyl;

(12) $R_3$ is hydrogen;

(13) $R_4$ is substituted aryl, where the substituents on the aryl are independently selected from one to three substituents selected from halogen, cyano, $C_1$-$C_4$alkyl, $C_1$-$C_4$alkoxy, $C_1$-$C_4$ alkoxycarbonyl, fluorinated $C_1$-$C_4$alkyl, fluorinated $C_1$-$C_4$alkoxy or $C_1$-$C_4$alkylsulfonyl;

(14) more preferably, $R_4$ is substituted aryl, where the substituents on the aryl are one to three halogen substituents;

(15) most preferably, $R_4$ is 4-fluorophenyl;

(16) $R_5$ is selected from amino, $C_1$-$C_6$alkylamino, $C_1$-$C_6$ dialkylamino, $C_3$-$C_8$cycloalkylamino, arylamino, ar$C_1$-$C_6$alkylamino, heteroalkyl$C_1$-$C_6$alkylamino, —N($C_1$-$C_6$alkyl)-$C_1$-$C_6$alkyl-N($C_1$-$C_6$alkyl)$_2$, heteroalkyl or substituted heteroalkyl wherein the substituent on the heteroalkyl is selected from oxo, amino, $C_1$-$C_6$alkoxy$C_1$-$C_6$ alkyl, $C_1$-$C_6$alkylamino or $C_1$-$C_6$ dialkylamino;

(17) preferably, $R_5$ is $C_1$-$C_6$alkylamino or $C_3$-$C_8$cycloalkylamino;

(18) m is one;

(19) n is one;

(20) p is 0; and combinations of (1) through (20) above.

Still another preferred embodiment of the present invention is directed to structurally novel compounds represented by the following general formula (IV):

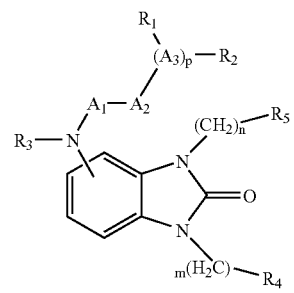

Formula (IV)

wherein $A_1$, $A_2$ and $A_3$ are each independently a D- or L-amino acid selected from the group consisting of alanine, β-alanine, arginine, homoarginine, cyclohexylalanine, citrulline, cysteine (optionally substituted with $C_1$-$C_4$alkyl, aryl, or ar$C_1$-$C_4$alkyl), 2,4-diaminobutyric acid (optionally substituted with acyl, $C_1$-$C_4$alkyl, aroyl, amidino, or MeC(NH)—), 2,3 diaminopropionic acid (optionally substituted with acyl, $C_1$-$C_4$alkyl, aroyl, amidino, or MeC(NH)—), glutamine, glycine, indanylglycine, lysine (optionally substituted with acyl, $C_1$-$C_4$alkyl, aroyl, MeC(NH)—), valine, methionine, proline, serine (optionally substituted with $C_1$-$C_4$alkyl, aryl, or ar$C_1$-$C_4$alkyl), homoserine (optionally substituted with $C_1$-$C_4$alkyl, aryl, or ar$C_1$-$C_4$alkyl), tetrahydroisoquinoline-3-COOH, threonine (optionally substituted with $C_1$-$C_4$alkyl, aryl, or ar$C_1$-$C_4$alkyl), ornithine (optionally substituted with acyl, $C_1$-$C_4$alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

$R_1$ and $R_2$ are each independently selected from hydrogen, $C_1$-$C_8$alkyl, ar($C_1$-$C_8$)alkyl, $C_1$-$C_8$alkoxycarbonyl, aryloxycarbonyl, ar($C_1$-$C_8$)alkoxycarbonyl, $C_1$-$C_8$alkylcarbonyl, arylcarbonyl, ar($C_1$-$C_8$)alkylcarbonyl, aminocarbonyl, $C_1$-$C_8$alkylaminocarbonyl, $C_1$-$C_8$dialkylaminocarbonyl, arylaminocarbonyl, diarylaminocarbonyl, ar($C_1$-$C_8$)alkylaminocarbonyl, diar($C_1$-$C_8$)alkylaminocarbonyl, heterocyclylcarbonyl, heteroaryl($C_1$-$C_8$)alkyl, heteroaryloxycarbonyl, heteroaryl($C_1$-$C_8$)alkoxycarbonyl, heteroarylcarbonyl, heteroaryl($C_1$-$C_8$)alkylcarbonyl, heteroarylaminocarbonyl, diheteroarylaminocarbonyl, heteroaryl($C_1$-$C_8$)alkylaminocarbonyl, diheteroaryl($C_1$-$C_8$)alkylaminocarbonyl, wherein said aryl, ar($C_1$-$C_8$)alkyl, heteroaryl and heteroaryl ($C_1$-$C_8$)alkyl are optionally substituted with one or more of halogen, $C_1$-$C_8$alkyl, $C_1$-$C_8$alkoxy hydroxy, cyano, amino, and nitro; $R_1$ and $R_2$ are covalently bonded to the N-terminus of $A_3$ when p is 0 or $A_2$ when p is 1;

Preferably $R_1$ is hydrogen;

Preferably, $R_2$ is selected from hydrogen, $C_1$-$C_8$alkyl, aryloxycarbonyl, ar($C_1$-$C_8$)alkoxycarbonyl, $C_1$-$C_8$alkoxycarbonyl, $C_1$-$C_8$alkylcarbonyl, ar($C_1$-$C_8$)alkylcarbonyl, arylaminocarbonyl, diarylaminocarbonyl, $C_1$-$C_8$alkylaminocarbonyl, $C_1$-$C_8$dialkylaminocarbonyl, ar($C_1$-$C_8$alkoxy)carbonyl, and heterocyclylcarbonyl, wherein said aryl, ar($C_1$-$C_8$)alkyl, heteroaryl and heteroaryl ($C_1$-$C_8$)alkyl are optionally substituted with one or more of halogen, $C_1$-$C_8$alkyl, and $C_1$-$C_8$alkoxy;

$R_3$ is selected from hydrogen or $C_1$-$C_8$ alkyl; preferably, $R_3$ is hydrogen;

$R_4$ is selected from unsubstituted or substituted aryl, ar$C_1$-$C_8$alkyl, $C_3$-$C_8$cycloalkyl, heteroaryl, or heteroaryl($C_1$-$C_8$) alkyl, where the substituents on the aryl, ar$C_1$-$C_8$alkyl, cycloalkyl, heteroaryl or heteroaryl($C_1$-$C_8$)alkyl, group are independently selected from one or more of halogen, nitro, amino, cyano, hydroxyalkyl, $C_1$-$C_8$alkyl, $C_1$-$C_8$alkoxy, hydroxy, $C_1$-$C_4$alkylcarbonyl, $C_1$-$C_8$alkoxycarbonyl, fluorinated $C_1$-$C_4$alkyl, fluorinated $C_1$-$C_4$alkoxy or $C_1$-$C_4$alkylsulfonyl;

Preferably, $R_4$ is selected from unsubstituted or substituted aryl, ar$C_1$-$C_6$alkyl, $C_3$-$C_6$cycloalkyl or heteroaryl, where the substituents on the aryl, aralkyl, cycloalkyl or heteroaryl group are independently selected from one to three substituents selected from halogen, cyano, $C_1$-$C_4$alkyl, $C_1$-$C_4$alkoxy, $C_1$-$C_4$ alkoxycarbonyl, fluorinated $C_1$-$C_4$alkyl, fluorinated $C_1$-$C_4$alkoxy or $C_1$-$C_4$alkylsulfonyl;

$R_5$ is selected from amino, $C_1$-$C_8$alkylamino, $C_1$-$C_8$dialkylamino, arylamino, ar$C_1$-$C_8$alkylamino, $C_3$-$C_8$cycloalkylamino, heteroalkyl$C_1$-$C_8$alkylamino, heteroalkyl$C_1$-$C_8$alkyl-N-methylamino, $C_1$-$C_8$dialkylamino ($C_1$-$C_8$)alkylamino, —N($C_1$-$C_8$alkyl)-$C_1$-$C_8$alkyl-N($C_1$-$C_8$alkyl)$_2$, —N($C_1$-$C_8$alkyl)($C_1$-$C_8$alkenyl), —N($C_1$-$C_8$alkyl)($C_3$-$C_8$cycloalkyl), heteroalkyl or substituted heteroalkyl wherein the substituent on the heteroalkyl is selected from oxo, amino, $C_1$-$C_8$alkoxy($C_1$-$C_8$)alkyl, $C_1$-$C_8$alkylamino or $C_1$-$C_8$dialkylamino;

Preferably, $R_5$ is selected from amino, $C_1$-$C_6$alkylamino, $C_1$-$C_6$ dialkylamino, $C_3$-$C_8$cycloalkylamino, arylamino, ar$C_1$-$C_6$alkylamino, heteroalkyl$C_1$-$C_6$alkylamino, —N($C_1$-$C_6$alkyl)-$C_1$-$C_6$alkyl-N($C_1$-$C_6$alkyl)$_2$, heteroalkyl or substituted heteroalkyl wherein the substituent on the heteroalkyl is selected from oxo, amino, $C_1$-$C_6$alkoxy$C_1$-$C_6$ alkyl, $C_1$-$C_6$alkylamino or $C_1$-$C_6$ dialkylamino;

m is an integer selected from 0, 1, 2 or 3;

n is an integer selected from 1 or 2;

p is an integer selected from 0 or 1; preferably, p is 0;

preferably, the point of attachment of —N($R_3$)-$A_1$-$A_2$-($A_3$)$_p$-$R_1$($R_2$) is the 5 or 6 position of the core heterocyclic ring; more preferably, the point of attachment is the 6 position; and enantiomers, diastereomers, tautomers, solvates, and pharmaceutically acceptable salts thereof.

Preferred compounds of formula (IV) are those wherein (1) $A_1$ is an unsubstituted or substituted amino acid residue selected from the group consisting of phenylalanine, cyclohexylalanine, alanine, β-alanine, heteroarylalanine, naphthylalanine, homophenylalanine, arylglycine, heteroarylglycine, aryl-β-alanine, and heteroaryl-β-alanine wherein the substituents on the amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

(2) more preferably, $A_1$ is an unsubstituted or substituted amino acid residue selected from the group consisting of phenylalanine, cyclohexylalanine, and heteroarylalanine, wherein the substituents on the amino acid are independently selected from one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

(3) even more preferably, $A_1$ is an unsubstituted amino acid residue selected from the group consisting of phenylalanine, cyclohexylalanine, and heteroarylalanine;

(4) most preferably, $A_1$ is phenylalanine or cyclohexylalanine;

(5) $A_2$ is an amino acid selected from the group consisting of arginine, homoarginine, 2,4-diaminobutyric acid (optionally substituted with acyl, $C_1$-$C_4$alkyl, aroyl, amidino, or MeC(NH)—), 2,3 diaminopropionic acid (optionally substituted with acyl, $C_1$-$C_4$alkyl, aroyl, amidino, or MeC(NH)—), glutamine, and lysine (optionally substituted with acyl, $C_1$-$C_4$alkyl, aroyl, amidino or MeC(NH)—);

(6) preferably, $A_2$ is an amino acid selected from the group consisting of arginine, homoarginine, 2,4-diaminobutyric acid, 2,3-diaminopropionic acid, glutamine, and lysine;

(7) more preferably, $A_2$ is arginine;

(8) $R_1$ is hydrogen;

(9) $R_2$ is selected from hydrogen, $C_1$-$C_8$alkyl, aryloxycarbonyl, $C_1$-$C_8$alkoxycarbonyl, $C_1$-$C_8$alkylcarbonyl, arylaminocarbonyl, diarylaminocarbonyl, $C_1$-$C_8$alkylaminocarbonyl, $C_1$-$C_8$dialkylaminocarbonyl, ar($C_1$-$C_8$alkoxy)carbonyl, and heterocyclylcarbonyl, wherein said aryl, ar($C_1$-$C_8$) alkyl, heteroaryl and heteroaryl($C_1$-$C_8$)alkyl are optionally substituted with one or more of halogen, $C_1$-$C_8$alkyl, and $C_1$-$C_8$alkoxy;

(10) more preferably, $R_2$ is selected from $C_1$-$C_8$alkylcarbonyl, aryloxycarbonyl, arylaminocarbonyl, and ar($C_1$-$C_8$alkoxy)carbonyl, wherein said aryl, ar($C_1$-$C_8$)alkyl, heteroaryl and heteroaryl($C_1$-$C_8$) alkyl are optionally substituted with one or more of halogen, $C_1$-$C_8$alkyl, and $C_1$-$C_8$alkoxy;

(11) most preferably, $R_2$ is selected from acetyl, Fmoc, and p-methoxyphenylaminocarbonyl;

(12) $R_3$ is hydrogen;

(13) $R_4$ is substituted aryl, where the substituents on the aryl are independently selected from one to three substituents selected from halogen, cyano, $C_1$-$C_4$alkyl, $C_1$-$C_4$alkoxy, $C_1$-$C_4$ alkoxycarbonyl, fluorinated $C_1$-$C_4$alkyl, fluorinated $C_1$-$C_4$alkoxy or $C_1$-$C_4$alkylsulfonyl;

(14) more preferably, $R_4$ is substituted aryl, where the substituents on the aryl are one to three halogen substituents;

(15) most preferably, R is 4-fluorophenyl;

(16) $R_5$ is selected from amino, $C_1$-$C_6$alkylamino, $C_1$-$C_6$ dialkylamino, $C_3$-$C_8$cycloalkylamino, arylamino, ar$C_1$-$C_6$alkylamino, heteroalkyl$C_1$-$C_6$alkylamino, —N($C_1$-$C_6$alkyl)-$C_1$-$C_6$alkyl-N($C_1$-$C_6$alkyl)$_2$, heteroalkyl or substituted heteroalkyl wherein the substituent on the heteroalkyl is selected from oxo, amino, $C_1$-$C_6$alkoxy$C_1$-$C_6$ alkyl, $C_1$-$C_6$alkylamino or $C_1$-$C_6$ dialkylamino;

(17) preferably, $R_5$ is $C_1$-$C_6$alkylamino or $C_3$-$C_8$cycloalkylamino;

(18) m is one;
(19) n is one;
(20) p is 0; and combinations of (1) through (20) above.

The compounds of the present invention are thrombin receptor antagonists and as such are useful in treating thrombosis, restenosis, hypertension, heart failure, arrhythmia, myocardial infarction, glomerulonephritis, reocclusion following thrombolytic therapy, reocclusion following angioplasty, inflammation, angina, stroke, atherosclerosis, ischemic conditions, a vaso-occlusive disorder, neurodegenerative disorders, angiogenesis and related disorders and cancer. These compounds are also useful as antithrombotics in conjunction with fibrinolytic therapy (e.g., t-PA or streptokinase).

In the compounds of formulae (I), (II), (III) and (IV), the amino acid residues comprising the $A_1$, $A_2$ and $A_3$ substituents are attached to the adjacent moiety so that the amino-terminus (N-terminus) of the amino acid is drawn on the right and the carboxy-terminus of the amino acid is drawn on the left. So, for example, in Compound 1, where $A_1$ is phenylalanine and $A_2$ is arginine, the carbonyl group of the phenylalanine residue is attached to the N($R_3$) group on the core ring and the amino terminus is attached to the carbonyl group of the second amino acid residue.

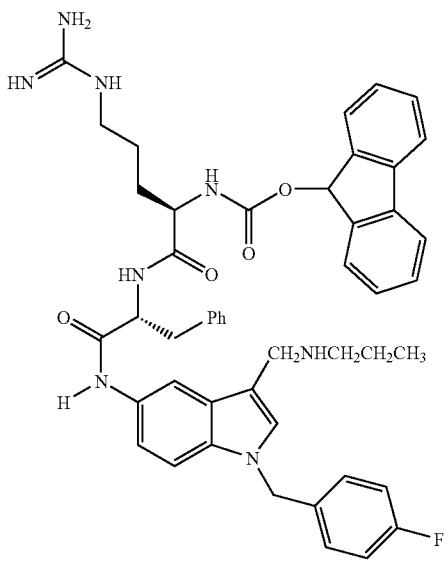

Compound 1

When a particular group is "substituted" (e.g., Phe, aryl, heteroalkyl, heteroaryl), that group may have one or more substituents, preferably from one to five substituents, more preferably from one to three substituents, most preferably from one-to two substituents, independently selected from the list of substituents.

Amino acid abbreviations are defined below:

| | |
|---|---|
| Ala | Alanine |
| β-Ala | beta-Alanine |
| Arg | Arginine |
| hArg | Homoarginine |
| Cha | Cyclohexylalanine |
| Cit | Citrulline |
| Cys | Cysteine |
| Dbu | 2,4-Diaminobutyric acid |
| Dpr | Diaminopropionic acid |
| Gln | Glutamine |
| Gly | Glycine |
| His | Histidine |
| Lys | Lysine |
| Met | Methionine |
| Nal | Naphthylalanine |
| Orn | Ornithine |
| Phe | Phenylalanine |
| hPhe | Homophenylalanine |
| Pro | Proline |
| Pyr-Ala | Pyridylalanine |
| Ser | Serine |
| hSer | Homoserine |
| Tic | Tetrahydroisoquinoline-3-COOH |
| Tyr | Tyrosine |
| Val | Valine |

Under standard nomenclature used throughout this disclosure, the terminal portion of the designated side chain is described first, followed by the adjacent functionality toward the point of attachment. Thus, for example, a "phenyl$C_1$-$C_6$ alkylamido$C_1$-$C_6$alkyl" substituent refers to a group of the formula

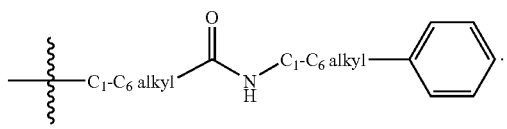

The compounds of the present invention may also be present in the form of a pharmaceutically acceptable salt. The pharmaceutically acceptable salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, unless otherwise noted "alkyl" and "alkoxy" whether used alone or as part of a substituent group, include straight and branched chains having 1 to 8 carbon atoms, or any number within this range. For example, alkyl radicals include methyl, ethyl, propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. Cycloalkyl groups contain 3 to 8 ring carbons and preferably 5 to 7 carbons. Similarly, alkenyl and alkynyl groups include straight and branched chain alkenes and alkynes having 1 to 8 carbon atoms, or any number within this range.

The term "aryl" as used herein refers to an unsubstituted or substituted aromatic group such as phenyl and naphthyl. The term "aroyl" refers to the group —C(O)-aryl.

The term "heteroalkyl" as used herein represents an unsubstituted or substituted stable three to seven membered monocyclic saturated ring system which consists of carbon atoms and from one to three heteroatoms selected from N, O or S, and wherein the nitrogen or sulfur heteroatoms may optionally be oxidized, and the nitrogen heteroatom may optionally be quaternized. The heteroalkyl group may be attached at any heteroatom or carbon atom which results in the creation of a stable structure. Examples of such heteroalkyl groups include, but are not limited to azetidinyl, piperidinyl, pyrrolidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl. Preferred heteroalkyl groups include pyrrolidinyl, piperidinyl, piperazinyl, morpholinyl, azetidinyl and tetrahydrothiazolyl.

The term "heteroaryl" as used herein represents an unsubstituted or substituted stable five or six membered monocyclic aromatic ring system or an unsubstituted or substituted nine or ten membered benzo-fused heteroaromatic ring system or bicyclic heteroaromatic ring system which consists of carbon atoms and from one to four heteroatoms selected from N, O or S, and wherein the nitrogen or sulfur heteroatoms may optionally be oxidized, and the nitrogen heteroatom may optionally be quaternized. The heteroaryl group may be attached at any heteroatom or carbon atom that results in the creation of a stable structure. Examples of heteroaryl groups include, but are not limited to pyridyl, pyridazinyl, thienyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl adeninyl or quinolinyl. Preferred heteroaryl groups include pyridyl, pyrrolyl, pyrazinyl, thiadiazolyl, pyrazolyl, thienyl, triazolyl and quinolinyl.

The term "aralkyl" means an alkyl group substituted with one, two or three aryl groups (e.g., benzyl, phenylethyl, diphenylmethyl, triphenylmethyl). Similarly, the term "aralkoxy" indicates an alkoxy group substituted with an aryl group (e.g., benzyloxy). The term aminoalkyl refers to an alkyl group substituted with an amino group (i.e., -alkyl-NH$_2$). The term "alkylamino" refers to an amino group substituted with an alkyl group (i.e., —NH-alkyl). The term "dialkylamino" refers to an amino group which is disubstituted with alkyl groups wherein the alkyl groups can be the same or different (i.e., —N-[alkyl]$_2$).

The term "acyl" as used herein means an organic radical having 1 to 6 carbon atoms (branched or straight chain) derived from an organic acid by removal of the hydroxyl group.

The term "oxo" refers to the group =O.

The term "carbonyl" refers to the group C(O).

The term "halogen" shall include iodine, bromine, chlorine and fluorine.

Whenever the term "alkyl" or "aryl" or either of their prefix roots appear in a name of a substituent (e.g., aralkyl, dialkylamino) it shall be interpreted as including those limitations given above for "alkyl" and "aryl." Designated numbers of carbon atoms (e.g., $C_1$-$C_6$) shall refer independently to the number of carbon atoms in an alkyl or cycloalkyl moiety or to the alkyl portion of a larger substituent in which alkyl appears as its prefix root.

As used herein, the term "phosgene equivalent" represents the class of carbonic acid derivatives which include 4-nitrophenyl chloroformate, phosgene or "COCl$_2$," phenyl chloroformate, triphosgene or "(CCl$_3$O)$_2$CO," carbonyldiimidazole, diethyl carbonate or diphenyl carbonate.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

As used herein, the term "composition" is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention.

Particularly preferred compounds of the present invention shown in Table 1 (compounds of formula (V)) and Table 2 (compounds of formula (VI)), as follows; the amino acids bear the "L" absolute configuration unless denoted otherwise.

TABLE 1

Indolyl Peptidomimetics As
Thrombin Receptor (PAR-1) Antagonists

Formula (V)

| Cmpd No. | $A_1$ | $A_2$ | $R_2$ | $R_5$ | $R_4$ |
|---|---|---|---|---|---|
| 1 | Phe | Arg | Fmoc | —NH(propyl) | 4-Fluorophenyl |
| 2 | Phe | Arg | Acetyl | —NH(propyl) | 4-Fluorophenyl |
| 3 | Phe | Arg | PhNHCO— | —NH(propyl) | 4-Fluorophenyl |
| 4 | Phe | Arg | Cbz | —NH(propyl) | 4-Fluorophenyl |
| 5 | Phe | Arg | (4-OMe)PhNHCO— | —NH(propyl) | 4-Fluorophenyl |
| 6 | Phe | Arg | morpholine-N-C(O)-C(CH3)- | —NH(propyl) | 4-Fluorophenyl |
| 7 | Phe | Arg | Acetyl | —NH(cyclopentyl) | 4-Fluorophenyl |
| 8 | Phe | Arg | (4-OMe)PhNHCO— | —NH(cyclopentyl) | 4-Fluorophenyl |
| 9 | Phe | Arg | Fmoc | —NH(cyclopentyl) | 4-Fluorophenyl |
| 10 | Phe | Arg | (4-Cl)PhNHCO— | —NH(propyl) | 4-Fluorophenyl |
| 11 | Phe | Arg | (4-F)PhNHCO— | —NH(propyl) | 4-Fluorophenyl |
| 12 | Phe | Arg | (4-OMe)PhNHCO— | —NH(cyclopentyl) | 4-Fluorophenyl |

TABLE 2

Indolyl Peptidomimetics As
Thrombin Receptor (PAR-1) Antagonists

Formula (VI)

| Cmpd No. | $A_1$ | $A_2$ | $R_2$ | $R_5$ | $R_4$ |
|---|---|---|---|---|---|
| 13 | Phe | Arg | Acetyl | —NH(cyclopentyl) | 4-Fluorophenyl |
| 14 | Phe | Phe | Acetyl | —NH(cyclopentyl) | 4-Fluorophenyl |
| 15 | Phe | Arg | H | —NH(cyclopentyl) | 4-Fluorophenyl |
| 16 | Phe | Arg | Fmoc | —NH(cyclopentyl) | 4-Fluorophenyl |

TABLE 2-continued

Indolyl Peptidomimetics As
Thrombin Receptor (PAR-1) Antagonists

Formula (VI)

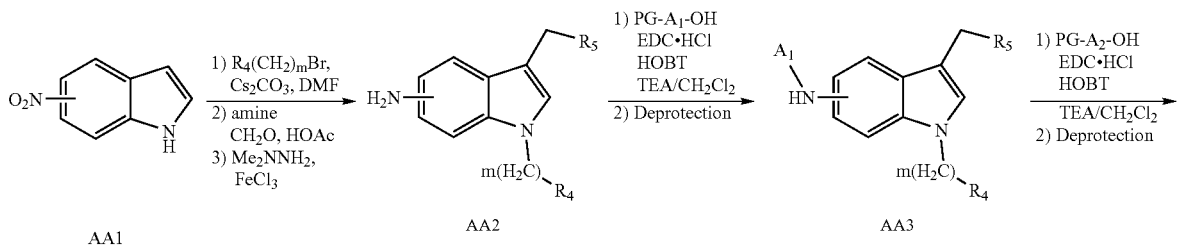

| Cmpd No. | $A_1$ | $A_2$ | $R_2$ | $R_5$ | $R_4$ |
|---|---|---|---|---|---|
| 17 | Phe | Arg | Benzyl-CO— | —NH(cyclopentyl) | 4-Fluorophenyl |
| 18 | Phe | Arg | (4-OMe)PhCH$_2$CO— | —NH(cyclopentyl) | 4-Fluorophenyl |
| 19 | Phe | Arg | Cbz | —NH(cyclopentyl) | 4-Fluorophenyl |
| 20 | Phe | Arg | Acetyl | —NH$_2$ | 4-Fluorophenyl |
| 21 | Cha | Arg | Acetyl | —NH(cyclopentyl) | 4-Fluorophenyl |

The antagonists of the present invention may be prepared via either solution-phase or solid-phase methods. All compounds presented in Table 1 and Table 2 may be prepared using the methodology outlined in generic schemes AA through DD.

SCHEME AA

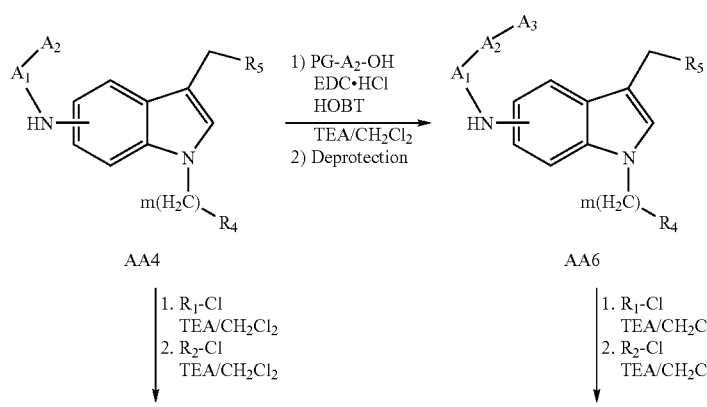

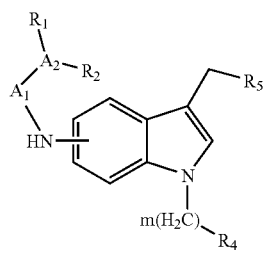

AA5

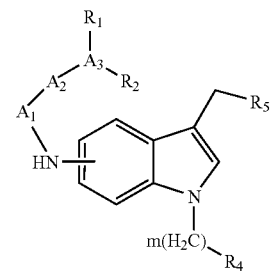

AA7

Nitroindole AA1 was alkylated with an appropriately substituted alkyl or arylalkyl halide in the presence of a base such as cesium carbonate, potassium carbonate and the like also in the presence of a solvent such as DMF to provide a 1-substituted indole intermediate. The resulting intermediate was reacted with an amine such as pyrrolidine, piperidine and the like while dissolved in an organic acid such as glacial acetic acid in the presence of formaldehyde also in glacial acetic acid to provide a 3-substituted indole intermediate. The nitro group of the resulting intermediate was then reduced to an amino group by reaction with 1,1-dimethylhydrazine in the presence of an alcohol solvent such as MeOH and charcoal and ferric chloride hexahydrate which provided intermediate AA2.

Intermediate AA2 was coupled to an appropriately protected amino acid $A_1$ using standard peptide coupling conditions well known to those skilled in the art. An example of such conditions include reacting the amino indole with the amino acid $A_1$ in the presence of a solvent such as DCM, also in the presence of a peptide coupling reagent such as EDC, DCC and the like, also in the presence of standard coupling reaction additives such as HOBT, and also in the presence of a non-nucleophilic amine such as TEA, DIPEA and the like. The protecting group on the amino acid is then removed using conditions well known to those skilled in the art. An example of such conditions include treatment of a Boc-protected amino acid derivative with a solution of a strong acid such as TFA, HCl and the like in an appropriate solvent such as $CH_2Cl_2$ or treatment of an Fmoc protected amino acid derivative with an organic base such as piperidine in an appropriate solvent such as dioxane. This reaction sequence gives rise to intermediate AA3.

The substituent $R_3$ may be introduced at this stage by reacting intermediate AA3 with an alkyl halide $R_3$—X such as methyl iodide, ethyl bromide and the like in the presence of a strong base such as NaH and the like, also in the presence of an appropriate solvent such as DMF and the like. Other standard alkylation conditions well known to those skilled in the art may also be used to introduce substituent $R_3$. Alternatively, $R_3$ may remain hydrogen.

The peptide coupling/deprotection sequence described above may be performed in an iterative manner which provides intermediates AA4 and AA6. These intermediates may be subsequently functionalized with $R_1$ and $R_2$ substituents upon reaction of the terminal amino group with an electrophilic agent such as an alkyl halide, an acyl halide, an aryl ($C_1$-$C_6$)alkyl halide and the like to provide target compounds AA5 and AA7.

Scheme BB

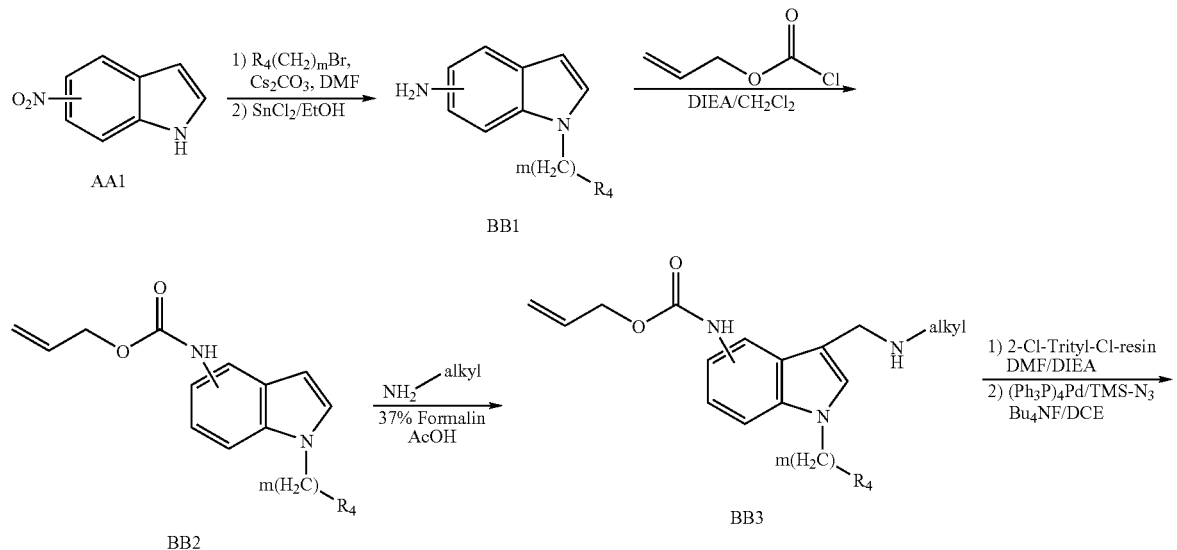

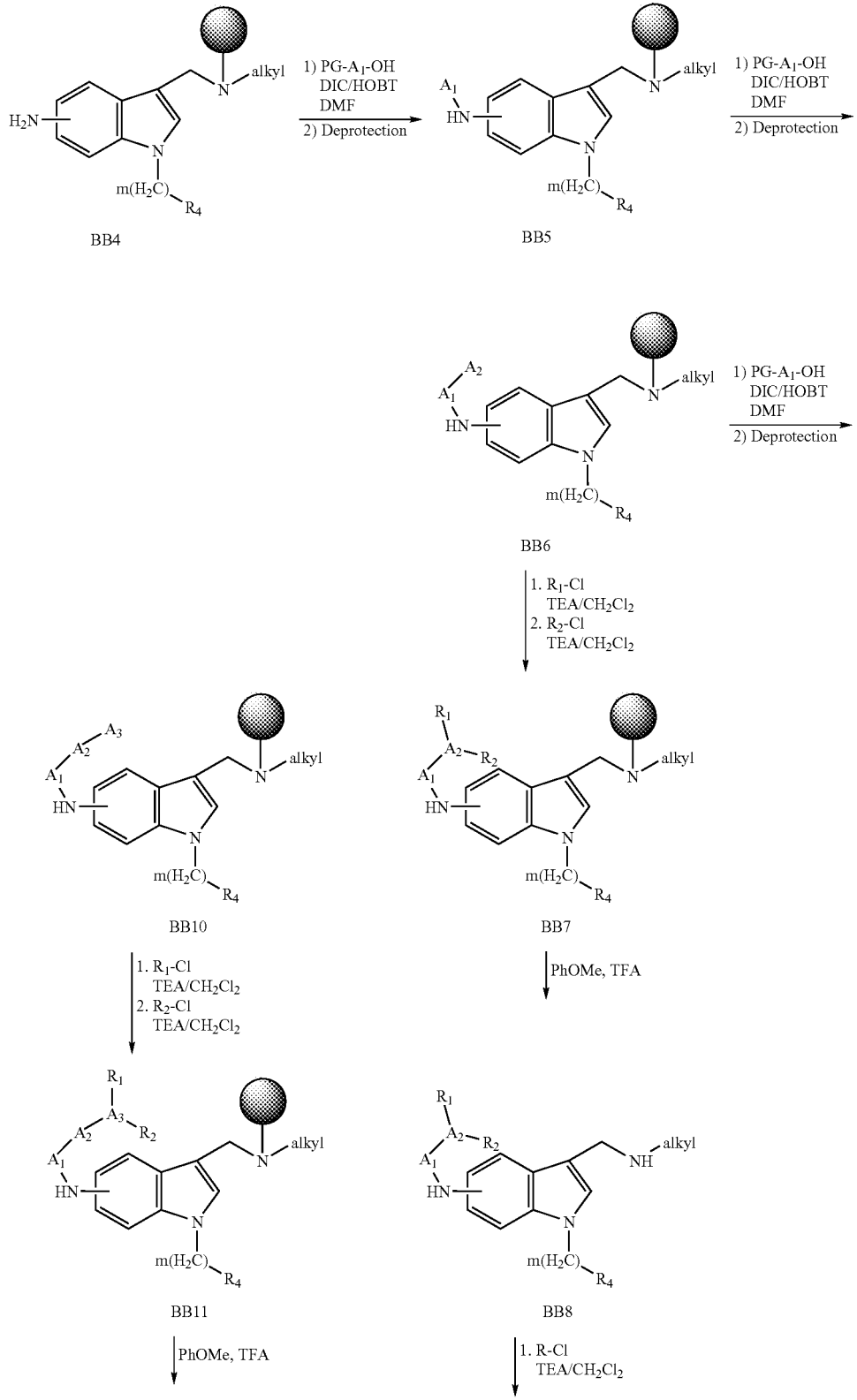

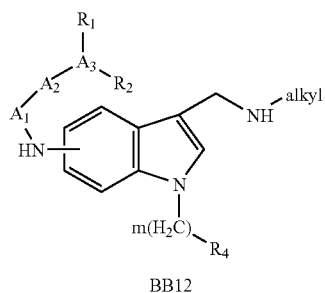

BB12

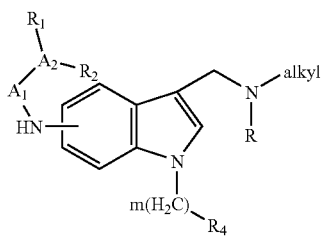

BB9

1. R-Cl
TEA/CH₂Cl₂ ↓

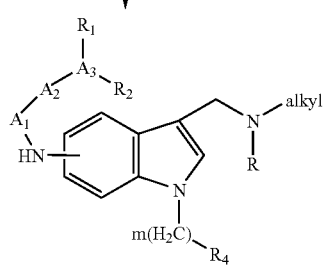

BB13

Nitroindole AA1 was alkylated with an appropriately substituted alkyl or aryl($C_1$-$C_6$)alkyl halide in the presence of a base such as cesium carbonate, potassium carbonate and the like also in the presence of a solvent such as DMF to provide a 1-substituted indole intermediate. The nitro group of the resulting intermediate was then reduced to an amino group by reaction with $SnCl_2$ in the presence of an alcohol solvent such as MeOH to provide intermediate BB1. The resulting amino group was protected using conditions known to those skilled in the art which provided intermediate BB2.

Intermediate BB2 then can undergo a Mannich-type reaction with an alkyl amine in the presence of formalin and an acid like AcOH to give intermediate BB3. The 3-substituted indole BB3 is then attached to a trityl resin and the amino substituent on the indole ring is deprotected which gives rise to intermediates BB4. Both reactions are performed using methodology well known to those skilled in the art as illustrated in the scheme.

Intermediate BB4 is then subjected to an iterative sequence of amino acid coupling/deprotection as described before relative to Scheme AA to give intermediates BB5, BB6, and BB10. In any of these three amino acid coupled intermediates, the $R_3$ substituent may be introduced before deprotection of the terminal amino group by alkylation reactions known to those skilled in the art and discussed previously as related to Scheme AA. Alternatively, $R_3$ may remain hydrogen.

Intermediates BB10 and BB6 may be further functionalized with R, and/or $R_2$ substituents in the same manner as described in Scheme AA for intermediates AA4 and AA6. Following the addition of the $R_1$ and/or $R_2$ substituents, the molecules are cleaved from the trityl resin by treatment with anisole in TFA, a procedure well known to those skilled in the art. This cleavage gives rise to targets BB8 and BB12.

The 3-indole substituent in targets BB6 and BB12 may be further functionalized at the —NH site by reaction with an appropriate alkyl halide, alkenyl halide, or cycloalkyl halide and the like under conditions known to those skilled in the art to provide additional targets BB9 and BB13.

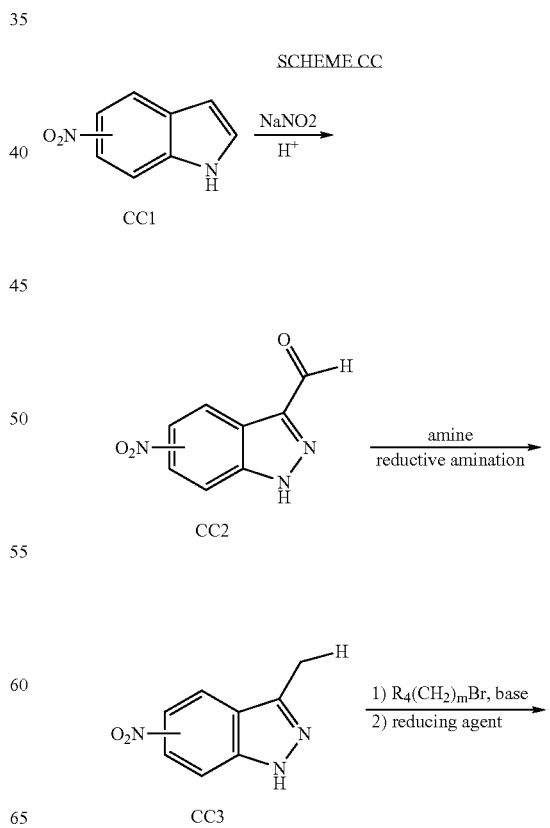

-continued

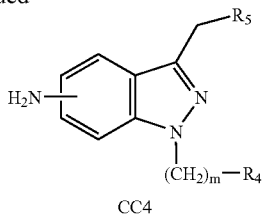

CC4

An appropriately nitro substituted indole CC1 (Scheme CC) was treated with aqueous NaNO$_2$ under acidic conditions (pH from about pH 1 to about pH 2) to give (via nitrosation, G. Buchi, *J. Am. Chem. Soc.* 1986, 108, 4115) 3-indazolecarboxaldehyde CC2. Reductive amination of CC2 with an amine such as pyrrolidine and a reducing agent such as sodium triacetoxyborohydride introduced the R$_5$ group and afforded CC3. Alkylation of CC3 with a substituted aralkyl or heteroarylalkyl halide and a base such as potassium hydroxide in an aprotic solvent such as THF to give an intermediate, which was reduced in a classical manner with, for example, iron and acetic acid or with a newer method such as dimethyl hydrazine and iron to give aminoindazole intermediate CC4.

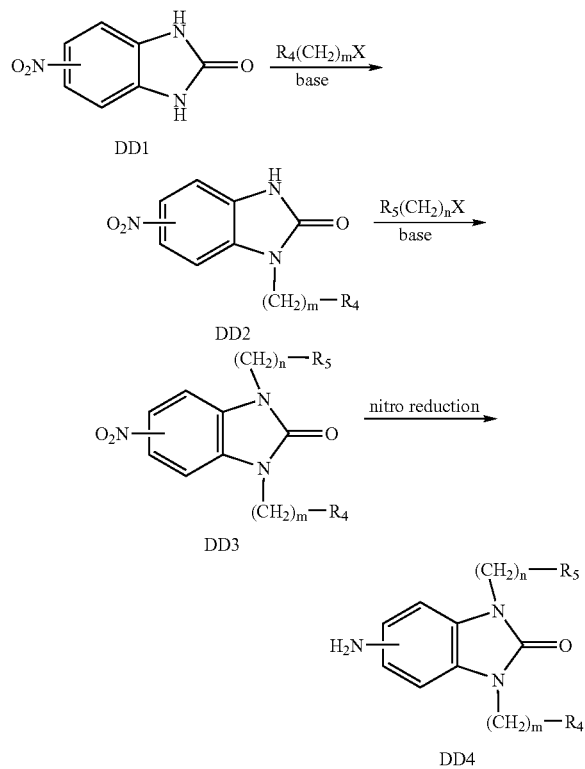

An appropriately nitro substituted benzimidazolone DD1 (Scheme DD) was alkylated with a substituted aralkyl or heteroaryl alkyl halide and a base such as sodium hydride in a dipolar aprotic solvent such as DMF to give DD2 as a mixture of two regioisomers. Two isomers were separated by silica gel column and then alkylated, with an aminoalkyl halide and a base such as sodium hydride in a dipolar aprotic solvent such as DMF to give two regioisomers DD3, respectively. Reduction of nitro group in DD3 in a classical manner with for example iron and acetic acid or with a newer method such as dimethyl hydrazine and iron to give aminobenzimidazolone intermediate DD4.

The aminoindazoles CC4 and the aminobenzimidazolones DD4 may be subjected to the same peptide coupling/deprotection sequences and the reactions used to introduce R$_1$, R$_2$ and R$_3$ as described in previous schemes which will provide additional compounds of Formula (I).

The utility of the compounds to treat PAR-1 mediated disorders (e.g., thrombotic disorders) can be determined according to the procedures described herein. The present invention therefore provides a method of treating PAR-1 mediated disorders (e.g., thrombotic disorders) in a subject in need thereof which comprises administering any of the compounds as defined herein in a quantity effective to treat PAR-1 mediated disorders. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.03 mg/kg to about 100 mg/kg (preferred from about 0.1 mg/kg to about 30 mg/kg) of a compound of the present invention and may be given at a dosage from about 0.1 mg/kg/day to about 300 mg/kg/day (preferred from about 1 mg/kg/day to about 50 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums and other pharmaceutical diluents, e.g. water, to form a solid preformulation composition containing a homogeneous mixture of a compound of the present invention or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The method of treating PAR-1 mediated disorders (e.g., thrombotic disorders) described in the present invention may also be carried out using a pharmaceutical composition comprising any of the compounds as defined herein and a pharmaceutically acceptable carrier. The pharmaceutical composition may contain between about 0.01 mg to about 100 mg, preferably from about 5 to about 50 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of PAR-1 mediated disorders is required.

The daily dosage of the products may be varied over a wide range from about 0.01 mg to about 1,000 mg per adult human per day. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250 and 500 mg of the active ingredient for the symptomatic adjustment of the dosage to the patient to be treated. An effective amount of the drug is ordinarily supplied at a dosage level of from about 0.01 mg/kg to about 100 mg/kg of body weight per day. Preferably, the range is from about 0.03 mg/kg to about 10 mg/kg of body weight per day. The compounds may be administered on a regimen of about 1 time to about 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

Biology

The compounds of the present invention are thrombin receptor (PAR-1) antagonists. The compounds interrupt platelet activation induced by thrombin's proteolytic cleavage of its platelet surface receptor, and thereby inhibit platelet aggregation. Such compounds are, therefore, useful in treating platelet-mediated thrombotic disorders (e.g., arterial and venous thrombosis, acute myocardial infarction, reocclusion following thrombolytic therapy and angioplasty, and a variety of vaso-occlusive disorders) and other PAR-1 mediated disorders.

In Vitro Thrombin Receptor Binding Assay

CHRF membranes (Jones, *Biochim. Biophys. Acta* 1992, 1136, 272) are thawed from −70° C., centrifuged at maximum speed for 5 min, washed twice with binding buffer (50 mM HEPES containing 5 mM $MgCl_2$ and 0.1% BSA), and resuspended in binding buffer (25 μg/100 mL). 100 μL of membranes are added to the 24-Wallac plates and delivered to the Tomtech apparatus. In a typical experiment, 6 μL of samples (from a 125 μg/mL intermediary plate, 20% DMSO) and 44 μL buffer are delivered to the plates (final conc. of compounds is 3.7 μg/mL, 0.6% DMSO). Similarly, 6 μL 20% DMSO and 44 μL buffer are delivered to both column 1 (NSB) and column 12 (TB). 10 μL Ser-pFPhe-Har-Leu-Har-Lys-Tyr-$NH_2$ (721-40; 500 μM in deionized water) is added to column 1. 50 μL tritiated 721-40 (specific activity 46 Ci/mmol) is added to all the wells. The plates are mixed well for 20 seconds, incubated for 30 min, and then harvested with 10 mM HEPES/138 mM NaCl using the Skatron harvester. The filters (GF/C Brandel FPXLR 296) are presoaked 3 h in 0.5% polyethylenimine in HEPES/0.1M N-acetylglucosamine) are set in saran wrap and dried for 3 min in the microwave, and placed in sample bags (Wallac 1450-432). 4.5 mL scintillation fluid (Wallac, Betaplate Scint 1205-440) is added. The bags are sealed, placed in filter cassettes (Wallac 1450-104), and analyzed on the microbeta counter.

In Vitro Inhibition Of Thrombin- and SFLLRN-$NH_2$-Induced Gel-Filtered Platelet Aggregation Assay Platelet Rich Plasma concentrate (Biological Specialties, Inc) is gel filtered (Sepharose 2B, Pharmacia) in Tyrode's buffer (140 mM NaCl, 2.7 mM KCl, 12 mM $NaHCO_3$, 0.76 mM $Na_2HPO_4$, 5.5 mM dextrose, 5.0 mM Hepes, and 2 mg/ml BSA @ pH 7.4). The gel-filtered platelets are diluted with Tyrode's buffer (143,000 platelets/μl, final platelet count per well), compound solution in buffer, and 2 mM $CaCl_2$ in a 96 well plate. Platelet aggregation is initiated by the addition of human α-thrombin (American Diagnostica, 0.113 nM-0.187 nM) or SFLLRN-$NH_2$ (2 μM) shown to achieve 80% aggregation (0.015-0.025 NIH U/ml, 0.113 nM-0.187 nM). The assay plate is stirred constantly. Platelet aggregation is monitored by intermittently placing the plate in a microplate reader (Molecular Devices) to read optical density (650 nM, ΔSOFT) at 0 and 5 minutes after the thrombin addition. Aggregation was calculated to be the decrease in optical density between the time 0 and 5 minute measurements. All samples were tested in duplicate wells on the same plate.

Table 3 shows the biological activity of the compounds of the present invention. Table 3 contains $IC_{50}$ values (μM) of the compounds against platelet aggregation stimulated by thrombin and $IC_{50}$ values (μM) in a thrombin receptor (PAR-1) binding assay.

TABLE 3

Biological Activity

| Cmpd No. | Platelet Aggregation Thrombin $IC_{50}$ (μM) | Platelet Aggregation SFLLRN-NH2 $IC_{50}$ (μM) | Thrombin Receptor Binding $IC_{50}$ (μM) |
|---|---|---|---|
| 1 | 51.6 | 43.7 | |
| 2 | 80 | 3.2 | |
| 3 | | | >100 |
| 4 | | | 42 |
| 5 | | | >100 |
| 6 | | | >100 |
| 7 | | | |
| 8 | | | 75.4 |
| 9 | | | 88.6 |
| 10 | | | >100 |
| 11 | | | >100 |
| 12 | 37.3 | 5.3 | 20 |
| 13 | 50.1 | 4 | 5.2 |
| 14 | 92 | 2.6 | 4.8 |
| 15 | | | >100 |
| 16 | 15.6 | 1.8 | 7.6 |
| 17 | 44.5 | 9.8 | 10.4 |
| 18 | 61.7 | 16.4 | 11.7 |
| 19 | 18.7 | 11.1 | 2.4 |
| 20 | | | >100 |
| 21 | 4.7 | 3.2 | 10.7 |

EXAMPLES

General Procedures: Resins and protected amino acids were purchased from Novabiochem, Bachem Bioscience, Advanced ChemTech or Synthe Tech. All other chemicals were obtained from commercial suppliers and used without further purification. $^1$H and $^{13}$C NMR spectra were recorded on a Bruker AC 300B (300 MHz proton) or a Bruker AM-400 (400 MHz proton) spectrometer with Me$_4$Si as an internal standard (s=singlet, d=doublet, t=triplet, br=broad). APCI-MS and ES-MS were recorded on a VG Platform II mass spectrometer; methane was used for chemical ionization, unless noted otherwise. Accurate mass measurements were obtained by using a VG ZAB 2-SE spectrometer in the FAB mode. TLC was performed with Whatman 250-μm silica gel plates. Preparative TLC was performed with Analtech 1000-μm silica gel plates. Flash column chromatography was conducted with flash column silica gel (40-63 μm) and column chromatography was conducted with standard silica gel. HPLC separations were carried out on three Waters Prep-Pak® Cartridges (25×100 mm, Bondapak® C18, 15-20 μm, 125 Å) connected in series; detection was at 254 nm on a Waters 486 UV detector. Analytical HPLC was carried out on a Supelcosil ABZ+PLUS column (5 cm×2.1 mm), with detection at 254 nm on a Hewlett Packard 1100 UV detector. Microanalysis was performed by Robertson Microlit Laboratories, Inc.

In the examples and throughout this application, the following abbreviations have the meanings recited hereinafter:

| | |
|---|---|
| Ac | Acetyl |
| ACN | Acetonitrile |
| Bn | Benzyl |
| Boc | t-Butoxycarbonyl |
| Cbz | Carbobenzyloxy |
| DCC | 1,3-Dicyclohexylcarbodiimide |
| DCE | 1,2-Dichloroethane |
| DCM | Dichloromethane |
| EDC | 1-(3-Dimethylaminopropyl)-3-ethylcarbodiimide |
| DIC | Diisopropylcarbodiimide |
| DIEA | Diisopropylethylamine |
| DMF | N,N-Dimethylformamide |
| Et | Ethyl |
| EtOAc | Ethyl acetate |
| Fmoc | 9-Fluorenylmethoxycarbonyl |
| h | Hour |
| HBTU | 2-(1H-Benzotriazole-1-yl)-1,1,3,3-tetramethyluronium hexafluorophosphate |
| HOAc | Acetic acid |
| HOBT | Hydroxybenzotriazole |
| Me | Methyl |
| min | Minute |
| Pmc | 2,2,5,7,8-Pentamethylchroman-6-sulfonyl |
| rt | Room temperature |
| TEA | Triethylamine |
| THF | Tetrahydrofuran |
| TFA | Trifluoroacetic acid |
| TLC | Thin layer chromatography |

TLC Thin layer chromatopgraphy

Example 1

Synthesis of Compound 17 (Scheme AA)

5-Guanidino-2-phenylacetylamino-pentanoic acid {1-[1-(4-fluoro-benzyl)-3-pyrrolidin-1-ylmethyl-1H-indol-5-ylcarbamoyl]-2-phenyl-ethyl}-amide

SCHEME A

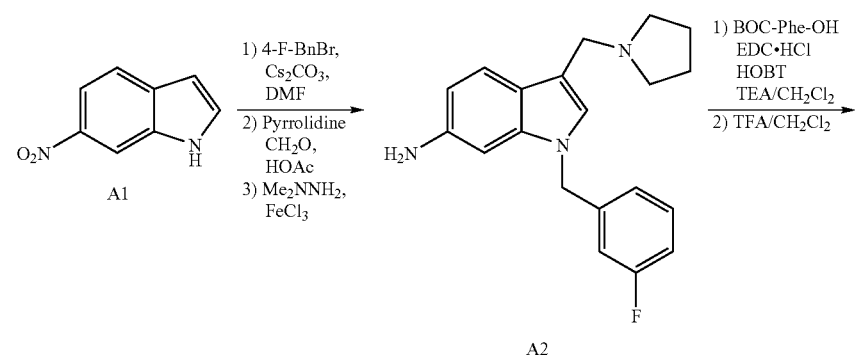

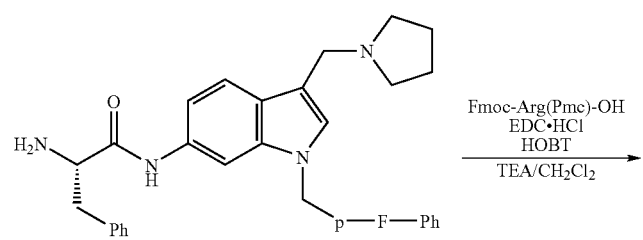

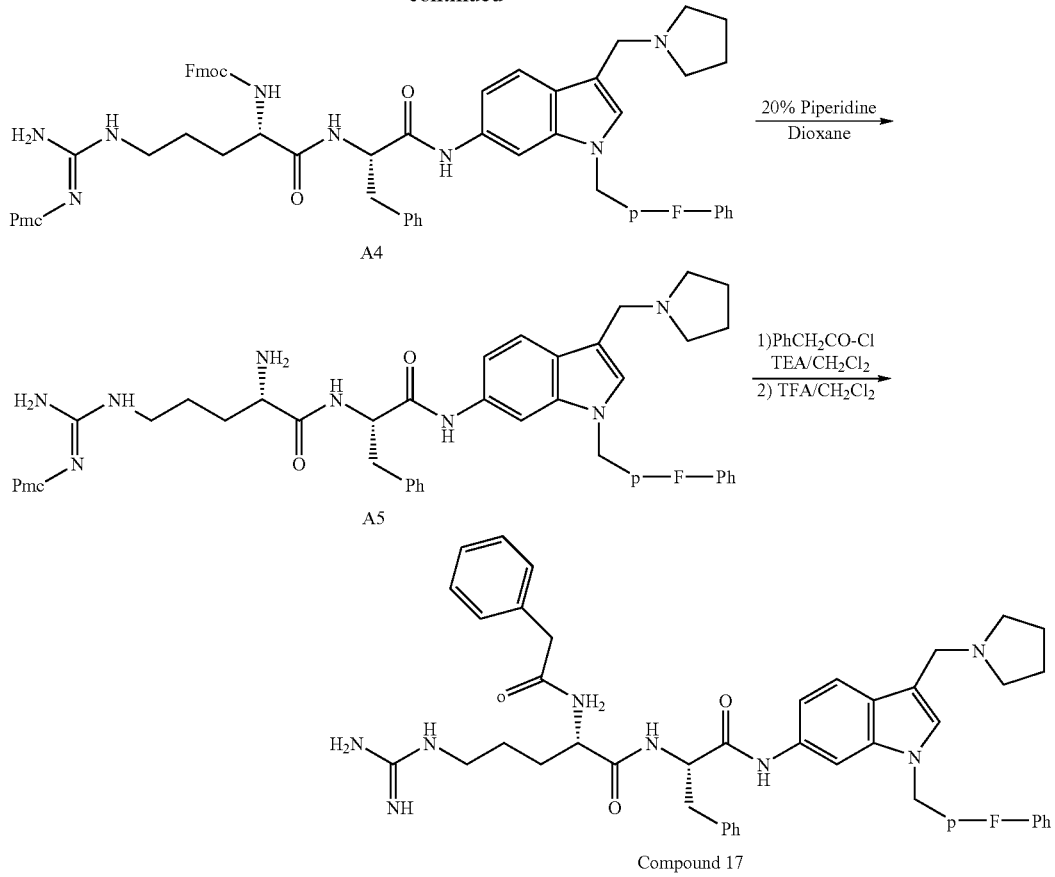

Compound 17

6Nitroindole A1 (6.57 g, 40.5 mmol) was dissolved in dry DMF under argon, cesium carbonate (13.2 g, 40.5 mmol) was added and the mixture was stirred at about 50° C. for about 30 min. After cooling to about rt, the mixture was stirred while 4-fluorobenzyl bromide (7.70 g, 40.7 mmol) in DMF was added dropwise; then the reaction was stirred at rt overnight. The solution was then partitioned between DCM and water. The organic layers were combined, washed with water, dried (MgSO$_4$) and evaporated in vacuo. The resulting residue dissolved in glacial acetic acid was added dropwise to a stirring solution of pyrrolidine (13.9 g, 195.4 mmol) and formaldehyde (37%, 15.9 g, 195.9 mmol) in glacial acetic acid and the reaction was stirred at rt overnight. The reaction pH. was brought to neutral by careful addition of 50% w/w NaOH. The mixture was extracted with DCM, washed with saturated NaHCO$_3$, dried (MgSO4) and evaporated in vacuo. The resulting solid was combined in MeOH with charcoal and ferric chloride hexahydrate (0.30 g, 1.1 mmol), 1,1-dimethylhydrazine (10.6 g, 176.6 mmol) was then added and the reaction was refluxed for about 16 h. After cooling to about rt, the reaction was filtered through dicalite and the filtrate was evaporated in vacuo to afford A2. ES-MS m/z 324 (MH$^+$).

To a solution of A2 (4.70 g, 14.5 mmol) in DCM, EDC-HCl (2.78 g, 14.5 mmol), HOBT (5 mg), TEA (1.5 g, 14.5 mmol), and BOC-Phe-OH (3.90 g, 14.5 mmol) were added; then the reaction was stirred at rt overnight. The reaction was extracted with saturated NH$_4$Cl and the organic layers were combined and evaporated in vacuo. This was purified by flash column chromatography using DCM/EtOH (95:5 to 90:10) to afford 3.45 g of a solid. The resulting solid (3.30 g, 5.78 mmol) was treated with TFA/CH$_2$Cl$_2$ (50/50) overnight at rt. The reaction was evaporated in vacuo and partitioned between DCM and saturated NaHCO$_3$. The organic layers were combined, filtered and evaporated in vacuo to give A3 (2.3 g). ES-MS m/z 471 (MH$^+$).

To a solution of A3 in DCM was added HOBT (5 mg), TEA (0.51 g, 5.0 mmol), and Fmoc-Arg(PMC)-OH (3.24 g, 4.89 mmol). EDC-HCl (0.94 g, 4.90 mmol) was added and the reaction stirred overnight at rt. The reaction was extracted with saturated NH$_4$Cl and the organic layers were combined and evaporated in vacuo. This was purified by flash column chromatography using DCM/MeOH (100:0 to 95:5) to afford 3.10 g of solid A4. ES-MS m/z 1116 (MH$^+$).

A4 was dissolved in 1,4-dioxane (16 mL) and piperidine (4 mL) was added and the reaction stirred for 3 h at rt. The reaction was evaporated in vacuo and triturated with ether/hexane to afford A5. ES-MS m/z 894 (MH$^+$).

To a solution of A5 (0.80 g, 0.90 mmol) and TEA (0.12 g, 1.2 mmol) in DCM was added a dropwise solution of phenylacetyl chloride (0.14 g, 0.90 mmol) in DCM and the reaction was stirred at rt overnight. The reaction was evaporated in vacuo and partitioned between DCM and saturated NH$_4$Cl. The organic layers were combined, evaporated in vacuo, and triturated with ether/hexane to give a solid which was treated with a solution (21 mL) of DCM:TFA:anisole (50:50:1) at rt overnight. The reaction was evaporated in vacuo and purified by reverse-phase HPLC to afford Compound 17. ES-MS m/z 745 (MH$^+$).

Example 2

Synthesis of Compound 19 (Scheme B)

(1-{1-[1-(4-Fluoro-benzyl)-3-pyrrolidin-1-ylmethyl-1H-indol-5-ylcarbamoyl]-2-phenyl-ethylcarbamoyl}-4-guanidino-butyl)-carbamic acid benzyl ester

SCHEME B

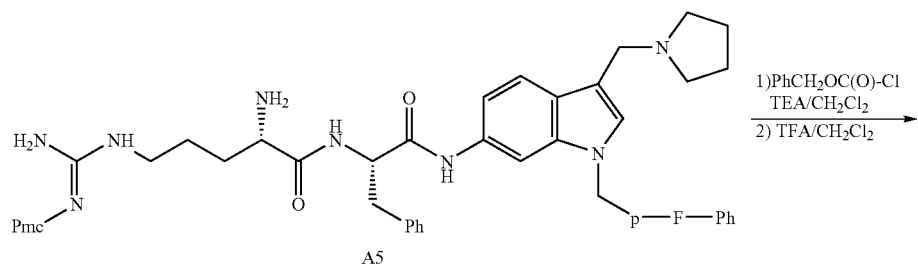

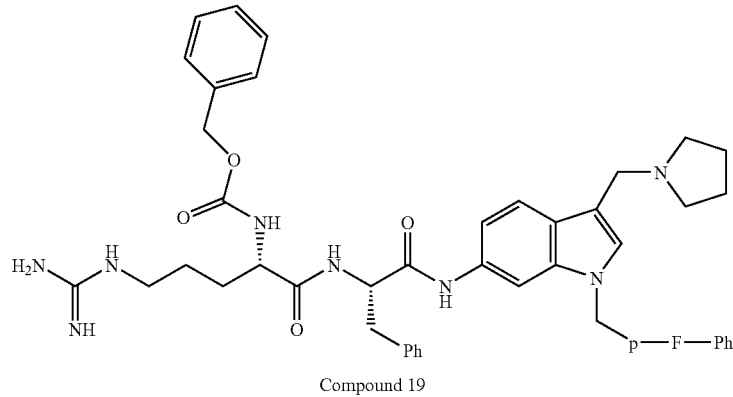

Compound 19

To a solution of A5 (0.50 g, 0.56 mmol) and TEA (0.07 g, 0.70 mmol) in DCM was added dropwise a solution of benzyl chloroformate (0.10 g, 0.56 mmol) in DCM and the reaction stirred at rt overnight. The reaction was evaporated in vacuo and partitioned between DCM and saturated $NH_4Cl$. The organic layers were combined, evaporated in vacuo, and triturated with ether/hexane to give a crude product which was purified by flash column chromatography using DCM/10-20% EtOH/1-2% $NH_4OH$) to afford 0.12 g of solid which was treated with a solution of DCM:TFA (50:50) at rt overnight. The reaction was evaporated in vacuo and purified by reverse-phase HPLC to afford Compound 19. ES-MS m/z 761 (MH$^+$). Anal. calcd. for $C_{43}H_{49}N_8O_4F.2.7C_2HF_3O_2$ (760.92/1068.78): C, 54.39; H, 4.88; N, 10.48; F, 16.18. Found: C, 54.87; H, 5.37; N, 9.87; F, 15.99.

Example 3

Synthesis of Compound 16 (Scheme BB)

(1-{1-[1-(4-Fluoro-benzyl)-3-pyrrolidin-1-ylmethyl-1H-indol-5-ylcarbamoyl]-2-phenyl-ethylcarbamoyl}-4-guanidino-butyl)-carbamic acid 9H-fluoren-9-ylmethyl Ester

SCHEME C

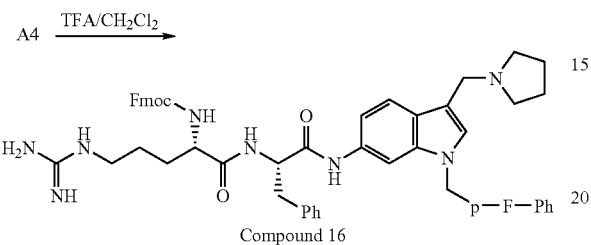

Compound 16

To a mixture of A4 (1.80 g, 1.6 mmol) and anisole (1.70 g, 15.7 mmol) was added TFA and the reaction was stirred at rt overnight. The reaction was evaporated in vacuo and partitioned between DCM and saturated $NaHCO_3$. The organic layers were combined, filtered and evaporated in vacuo. The crude product was purified by reverse-phase HPLC to give Compound 16. ES-MS m/z 849 (MH$^+$). Anal. calcd. for $C_{50}H_{53}N_8O_4F \cdot 2.5C_2HF_3O_2 \cdot 1.0H_2O$ (849.03/1152.10): C, 57.34; H, 5.03; N, 9.73; F, 14.02; KF, 1.56. Found: C, 56.98; H, 5.06; N, 9.69; F, 13.91; KF, 1.52.

Example 4

Synthesis of Compound 21 (Scheme D)

2-Acetylamino-5-guanidino-pentanoic acid {2-cyclohexyl-1-[1-(4-fluoro-benzyl)-3-pyrrolidin-1-ylmethyl-1H-indol-5-ylcarbamoyl]-ethyl}-amide

SCHEME D

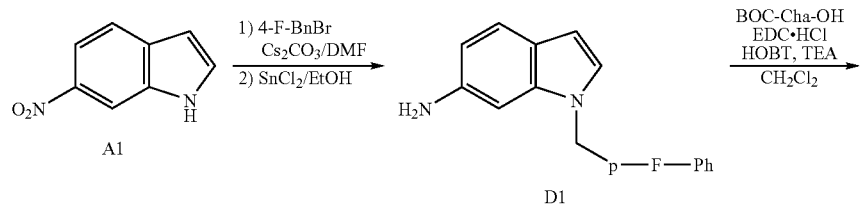

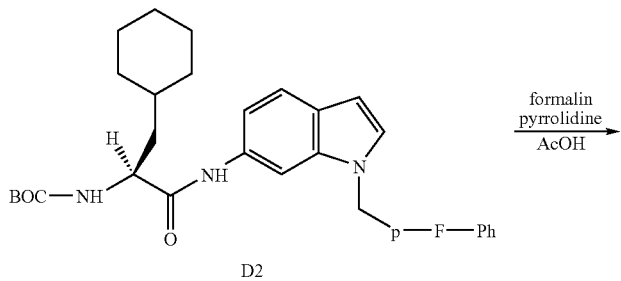

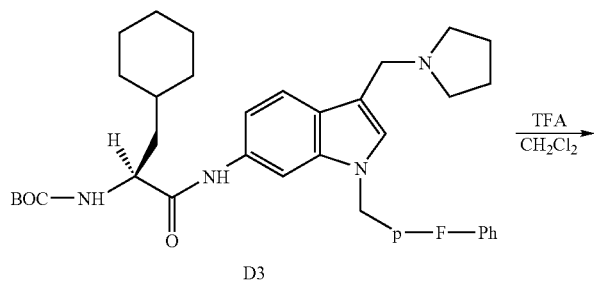

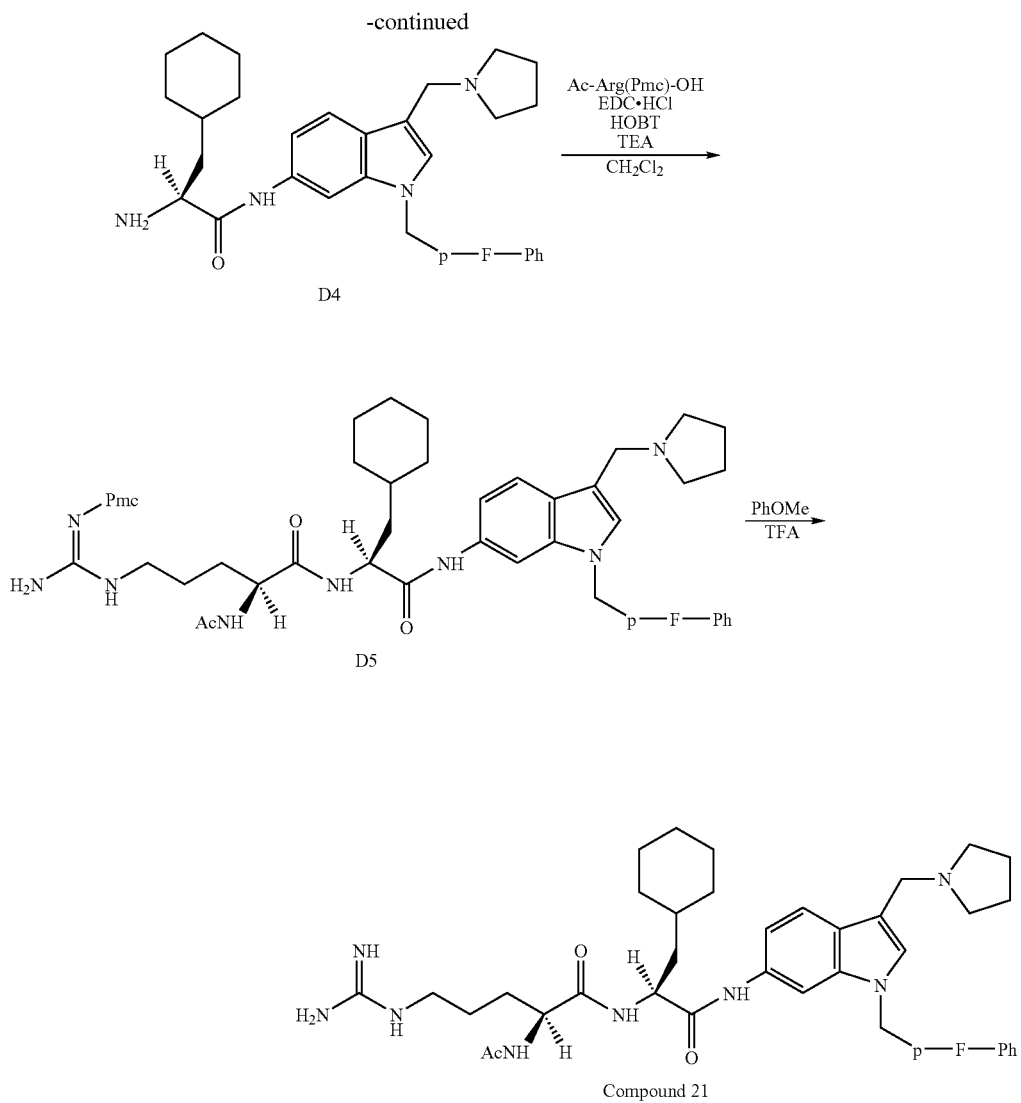

6-Nitroindole A1 (6.90 g, 42.5 mmol) was dissolved in dry DMF under argon, cesium carbonate (13.90 g, 42.6 mmol) was added and the mixture was stirred at about 50° C. for about 30 min. After cooling to about rt, the mixture was stirred while 4-fluorobenzyl bromide (8.10 g, 42.8 mmol) in DMF was added dropwise; then the reaction was stirred at rt overnight. The solution was then partitioned between DCM and water. The organic layers were combined, washed with water, dried ($MgSO_4$) and evaporated in vacuo. The resulting residue (10.0 g, 37.0 mmol) and tin (II) chloride (14.0 g, 73.8 mmol) were refluxed in ethanol overnight. The reaction was evaporated in vacuo. Saturated $NaHCO_3$ was added slowly to the remaining residue and the solution was stirred for 1 h. The solution was filtered and the collected solid was triturated with DCM. The DCM solution was evaporated in vacuo. The remaining residue was purified by flash column chromatography using $CH_2Cl$ to give 5.50 g of solid D1. ES-MS m/z 241 ($MH^+$).

To a solution of D1 (1.38 g, 5.7 mmol) in DCM, EDC.HCl (1.09 g, 5.7 mmol), HOBT (5 mg), TEA (0.58 g, 5.7 mmol), and N-BOC-Cha-OH (1.56 g, 5.7 mmol) were added. The reaction stirred overnight at rt. The reaction was extracted with saturated $NH_4Cl$ and the organic layers were combined and evaporated in vacuo. This was purified by flash column chromatography using DCM/MeOH (95:5) to afford 2.17 g of solid D2. ES-MS m/z 494 ($MH^+$).

A solution of D2 in glacial acetic acid was added dropwise to a stirring solution of pyrrolidine (1.40 g, 19.7 mmol) and formaldehyde (37%, 0.66 g, 8.1 mmol) in glacial acetic acid and the reaction was stirred at rt overnight. The reaction pH was brought to neutral by careful addition of 50% w/w NaOH. The mixture was extracted with DCM, washed with saturated $NaHCO_3$, dried (MgSO4) and evaporated in vacuo. The resulting residue was purified by column chromatography using acetone:EtOH:$NH_4OH$ (80:20:0.1) to give 1.2 g of solid D3 which was treated with TFA/$CH_2Cl_2$ (50/50) overnight at rt. The reaction was evaporated in vacuo and partitioned between DCM and saturated NaHCO$_3$. The organic layers were combined, filtered and evaporated in vacuo. ES-MS m/z 477 (MH$^+$).

To the remaining residue D4 in DCM was added HOBT (5 mg), TEA (0.20 g, 2.0 mmol), and Ac-Arg(PMC)-OH (0.95 g, 1.8 mmol). EDC.HCl (0.35 g, 1.8 mmol) was added and the reaction stirred overnight at rt. The reaction was extracted with saturated NH$_4$Cl and the organic layers were combined and evaporated in vacuo. The residue was purified by flash column chromatography using gradient DCM:MeOH:NH$_4$OH to give 0.43 g of solid D5 which was treated with a solution of anisole (0.25 g, 2.31 mmol) in DCM/TFA (4:1, 50 mL) at rt overnight. The reaction mixture was evaporated in vacuo and partitioned between DCM and water. The organic layers were combined and evaporated in vacuo to give the crude product. The crude product was purified by reverse-phase HPLC to give Compound 21. ES-MS m/z 675 (MH$^+$).

Example 5

Synthesis of Compound 2 (Scheme E)

2-Acetylamino-5-guanidino-pentanoic acid {1-[1-(4-fluoro-benzyl)-3-propylaminomethyl-1H-indol-5-ylcarbamoyl]-2-phenyl-ethyl}-amide

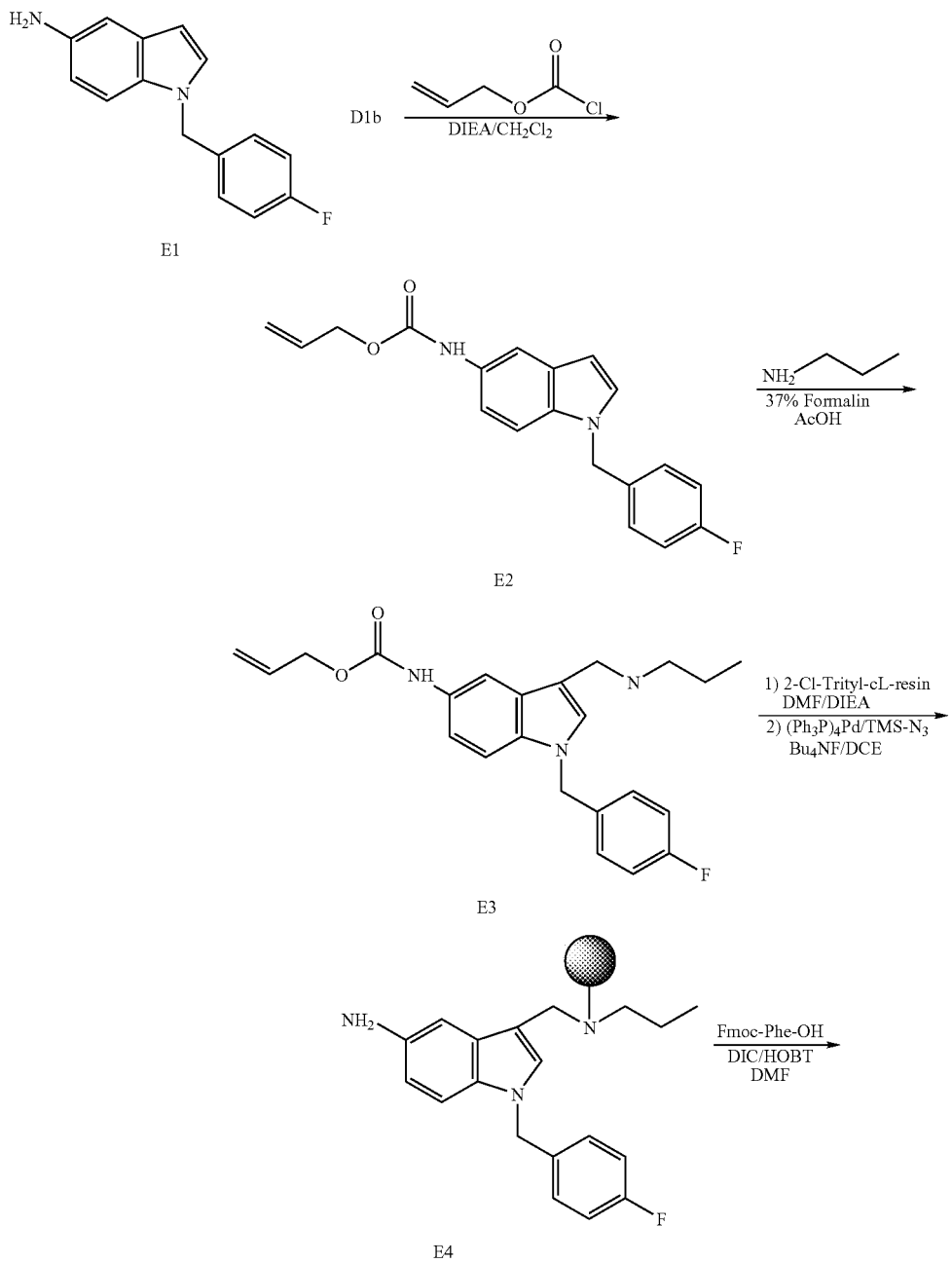

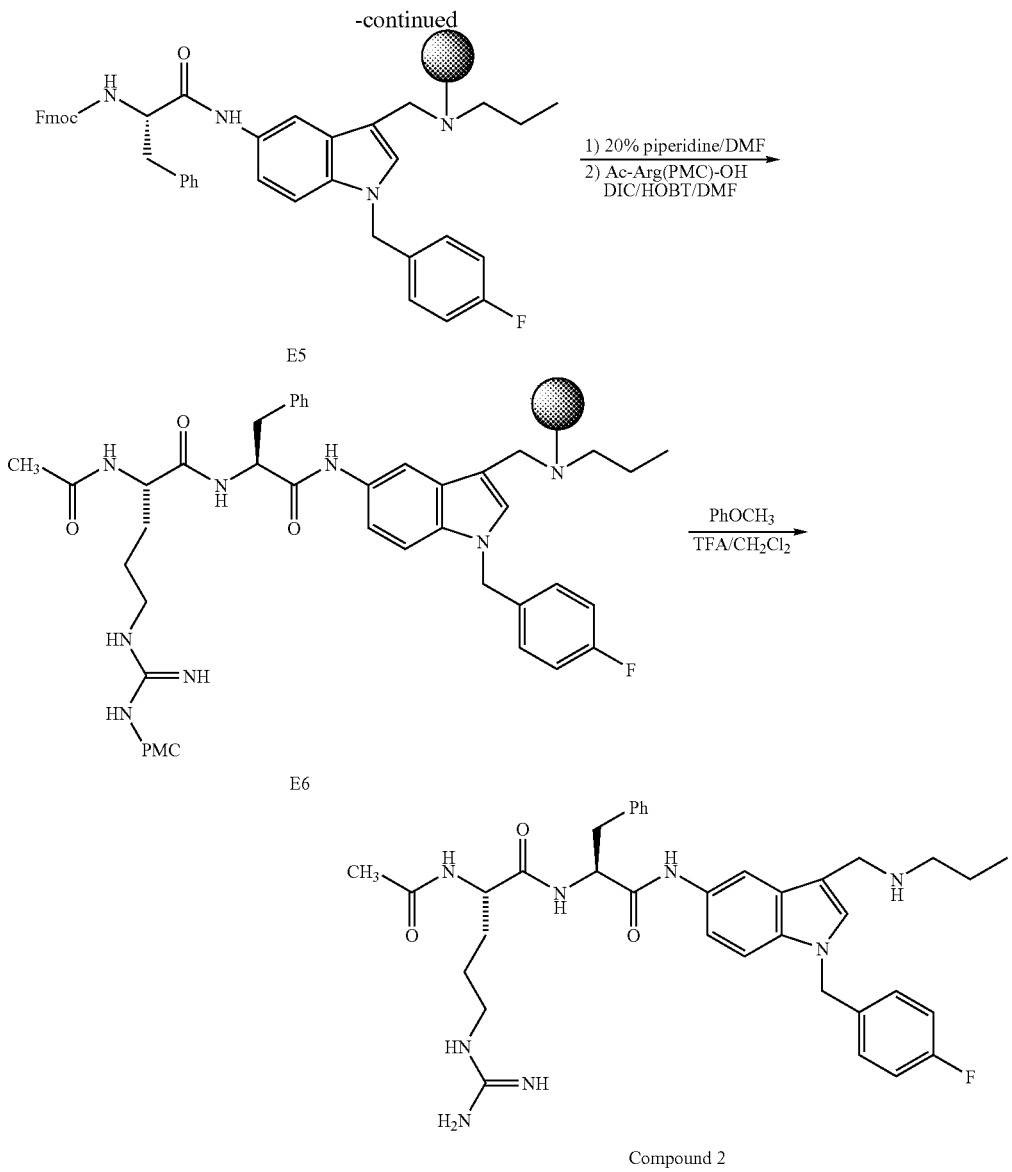

E5

E6

Compound 2

To a stirring solution of E1 (1.72 g, 7.1 mmol, prepared using the procedure for D1, see Scheme CC) and DIEA (1.25 mL, 7.2 mmol) in DCM (340 mL) was added dropwise a solution of allyl chloroformate (0.75 mL, 7.1 mmol) in DCM (100 mL). The reaction was stirred overnight at rt. The reaction was washed with $NH_4Cl$ (2×) and water (2×). The organic layer was dried ($MgSO_4$) and evaporated in vacuo. The resulting residue E2 was dissolved in glacial acetic acid and the solution was added dropwise to a stirring solution of propylamine (2.83 mL, 34.5 mmol) and formaldehyde (37%, 0.38 g, 13.8 mmol) in glacial acetic acid (46 mL), and the reaction was stirred at rt overnight. The reaction pH was brought to neutral by careful addition of 50% w/w NaOH. The mixture was extracted with DCM, washed with saturated $NaHCO_3$, dried (MgSO4) and evaporated in vacuo to give a crude product which was purified by flash column chromatograph using DCM:MeOH:$NH_4OH$ (97:3:1) to afford 1.16 g of E3.

2-Chlorotrityl chloride resin (0.27 g, 0.35 mmol; Novabiochem) was agitated (nitrogen bubbling) in a solid phase hourglass reactor in DMF (20 mL) as E3 (0.28 g, 0.70 mmol) and DIEA (0.30 mL, 1.70 mmoL) were added. The reaction was agitated at rt for about 21 h. The resin was washed with DMF (1×), DMF/$H_2O$ (1:4, 1×), DMF (3×), THF (3×), DCM (3×), and ether (1×). The resulting resin was agitated in DCE (25 mL) as $Bu_4NF.H_2O$ (0.27 g, 1.05 mmol), $TMSN_3$ (0.37 mL, 2.8 mmol) and $(Ph_3P)_4Pd$ (20 mol %, 0.08 g, 0.07 mmol) were added. The reaction was agitated at about rt for about 6 h. The resin was washed with DCE (2×), DMF/$H_2O$ (1:4, 1×), DMF (3×), THF (3×), and ether (1×) to give E4. A portion of the resin was cleaved with TFA/DCM (1:1) and the cleaved product was confirmed by ES-MS [m/z 312 ($MH^+$)].

Resin E4 was agitated in DMF (25 mL) with DIEA (0.18 mL, 1.05 mmol), Fmoc-Phe-OH (0.41 g, 1.05 mmol), HOBT (1.00 mg, cat. amount) and DIC (0.16 mL, 1.05 mmol ) for about 18 h. The solution was drawn off and the resin was washed with DMF (3×), THF (3×), DCM (4×) and ether (1×)

to afford E5. A portion of the resin was cleaved with TFA/DCM (1:1) and the cleaved product was confirmed by ES-MS [m/z 681 (MH$^+$)].

The resin E5 was combined with 20% piperidine in DMF (25 mL) and agitated for about 2 h. The solution was drained and the resin was washed with DMF (3×), THF (3×), and DCM (3×). The resulting resin was agitated in DMF (25mL) with DIEA (0.18 mL, 1.05 mmol), Ac-Arg(PMC)-OH (0.51 g, 1.05 mmol), HOBT (1,00 mg, cat. amount), and DIC (0.16 mL, 1.05 mmol) overnight. The solution was drawn off and the resin was washed with DMF (3×), THF (3×), DCM (4×) and ether (1×) to provide E6. A portion of the resin was cleaved with TFA/DCM (1:1) and the cleaved product was confirmed by ES-MS [m/z 923 (MH$^+$)].

The resin E6 was combined with anisole (0.08 mL, 0.70 mmol) in TFA/DCM (1:1, 50 mL) and agitated for 3 h. The solution was drawn off and the resin was washed with fresh 50% TFA/DCM; the filtrates were combined and evaporated. DCM was added to the remaining residue four times to azetrope off the TFA. The sample was triturated with ether (4×) to give the product Compound 2. ES-MS m/z 657 (MH$^+$).

As a specific embodiment of an oral composition, 100 mg of the Compound 17 of Example 1 is formulated with sufficient finely divided lactose to provide a total amount of about 580 mg to about 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:
1. A method of treating a condition selected from the group consisting of thrombosis, restenosis, hypertension, heart failure, arrhythmia, myocardial infarction, glomerulonephritis, reocclusion following thrombolytic therapy, reocclusion following angioplasty, inflammation, angina, stroke, atherosclerosis, ischemic conditions, a vaso-occlusive disorder in a subject in need thereof comprising administering to the subject a therapeutically effective amount of the compound of formula (I):

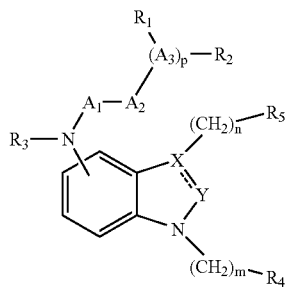

wherein
$A_1$, $A_2$ and $A_3$ are each independently a D- or L-amino acid selected from the group consisting of alanine, β-alanine, arginine, homoarginine, cyclohexylalanine, citrulline, cysteine (optionally substituted with $C_1$-$C_4$alkyl, aryl, or ar$C_1$-$C_4$alkyl), 2,4-diaminobutyric acid (optionally substituted with acyl, $C_1$-$C_4$alkyl, aroyl, amidino, or MeC(NH)—), 2,3 diaminopropionic acid (optionally substituted with acyl, $C_1$-$C_4$alkyl, aroyl, amidino, or MeC(NH)—), glutamine, glycine, indanylglycine, lysine (optionally substituted with acyl, $C_1$-$C_4$alkyl, aroyl, MeC(NH)—), valine, methionine, proline, serine (optionally substituted with $C_1$-$C_4$alkyl, aryl, or ar$C_1$-$C_4$alkyl), homoserine (optionally substituted with $C_1$-$C_4$alkyl, aryl, or ar$C_1$-$C_4$alkyl), tetrahydroisoquinoline-3-COOH, threonine (optionally substituted with $C_1$-$C_4$alkyl, aryl, or ar$C_1$-$C_4$alkyl), ornithine (optionally substituted with acyl, $C_1$-$C_4$alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, aryiglycine, heteroarylglycine, aryl-β-alanine, and heteroaryl-β-alanine wherein the substituents on the aromatic amino acid are independently one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;

$R_1$ and $R_2$ are each independently selected from the group consisting of hydrogen, $C_1$-$C_8$alkyl, ar($C_1$-$C_8$)alkyl, $C_1$-$C_8$alkoxycarbonyl, aryloxycarbonyl, ar($C_1$-$C_8$) alkoxycarbonyl, $C_1$-$C_8$alkylcarbonyl, arylcarbonyl, ar($C_1$-$C_8$)alkylcarbonyl, aminocarbonyl, $C_1$-$C_8$alkylaminocarbonyl, $C_1$-$C_8$dialkylaminocarbonyl, arylaminocarbonyl, diarylaminocarbonyl, ar($C_1$-$C_8$)alkylaminocarbonyl, diar($C_1$-$C_8$)alkylaminocarbonyl, heterocyclylcarbonyl, heteroaryl($C_1$-$C_8$)alkyl, heteroaryloxycarbonyl, heteroaryl($C_1$-$C_8$)alkoxycarbonyl, heteroarylcarbonyl, heteroaryl($C_1$-$C_8$)alkylcarbonyl, heteroarylaminocarbonyl, diheteroarylaminocarbonyl, heteroaryl($C_1$-$C_8$)alkylaminocarbonyl, and diheteroaryl-($C_1$-$C_8$)alkylaminocarbonyl wherein said aryl, ar($C_1$-$C_8$)alkyl, heteroaryl, and heteroaryl-($C_1$-$C_8$)alkyl are optionally substituted with one or more substituents which are halogen, $C_1$-$C_8$alkyl, $C_1$-$C_8$alkoxy, hydroxy, cyano, amino, or nitro;

$R_1$ and $R_2$ are covalently bonded to the N-terminus of $A_3$ when p is 1 or $A_2$ when p is 0;

$R_3$ is hydrogen or $C_1$-$C_8$alkyl;

$R_4$ is selected from the group consisting of unsubstituted or substituted aryl, ar$C_1$-$C_8$alkyl, $C_3$-$C_8$cycloalkyl, heteroaryl, and heteroaryl($C_1$-$C_8$)alkyl, where the substituents on the aryl, ar$C_1$-$C_8$alkyl, cycloalkyl, heteroaryl, or heteroaryl($C_1$-$C_8$)alkyl group are independently one or more of halogen, nitro, amino, cyano, hydroxyalkyl, $C_1$-$C_8$alkyl, $C_1$-$C_8$alkoxy, hydroxy, $C_1$-$C_4$alkylcarbonyl, $C_1$-$C_8$alkoxycarbonyl, fluorinated $C_1$-$C_4$alkyl, fluorinated $C_1$-$C_4$alkoxy, or $C_1$-$C_4$alkylsulfonyl;

$R_5$ is selected from the group consisting of amino, $C_1$-$C_8$alkylamino, $C_1$-$C_8$dialkylamino, arylamino, ar$C_1$-$C_8$alkylamino, $C_3$-$C_8$cycloalkylamino, heteroalkyl$C_1$-$C_8$alkylamino, heteroalkyl$C_1$-$C_8$alkyl-N-methylamino, $C_1$-$C_8$dialkylamino($C_1$-$C_8$)alkylamino, —N($C_1$-$C_8$alkyl)-$C_1$-$C_8$alkyl-N($C_1$-$C_8$alkyl)$_2$, —N($C_1$-$C_8$alkyl)($C_1$-$C_8$alkenyl), —N($C_1$-$C_8$alkyl)($C_3$-$C_8$cycloalkyl), heteroalkyl, and substituted heteroalkyl wherein the substituent on the heteroalkyl is oxo, amino, $C_1$-$C_8$alkoxy($C_1$-$C_8$)alkyl, $C_1$-$C_8$alkylamino, or $C_1$-$C_8$dialkylamino;

X is N or C;

Y is N, C, or —CO—;

provided that when Y is N, then X is C and there is a double bond between X and Y; provided also that when Y is C, then X is C and there is a double bond between X and Y; and provided also that when Y is —CO—, then X is N and there is a single bond between X and Y;
m is 0, 1, 2, or 3;
n is 1 or 2;
p is 0 or 1; and
enantiomers, diastereomers, tautomers, solvates, and pharmaceutically acceptable salts thereof.

2. A method of inhibiting platelet aggregation in a subject in need of treatment thereof comprising administering to the subject a therapeutically effective amount of the compound of formula (I):

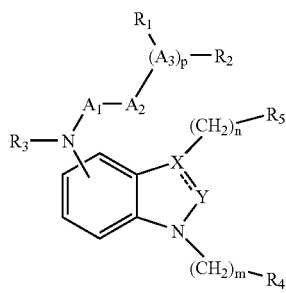

wherein
$A_1$, $A_2$ and $A_3$ are each independently a D- or L-amino acid selected from the group consisting of alanine, β-alanine, arginine, homoarginine, cyclohexylalanine, citrulline, cysteine (optionally substituted with $C_1$-$C_4$alkyl, aryl, or ar$C_1$-$C_4$alkyl), 2,4-diaminobutyric acid (optionally substituted with acyl, $C_1$-$C_4$alkyl, aroyl, amidino, or MeC(NH)—), 2,3 diaminopropionic acid (optionally substituted with acyl, $C_1$-$C_4$alkyl, aroyl, amidino, or MeC(NH)—), glutamine, glycine, indanylglycine, lysine (optionally substituted with acyl, $C_1$-$C_4$alkyl, aroyl, MeC(NH)—), valine, methionine, proline, serine (optionally substituted with $C_1$-$C_4$alkyl, aryl, or ar$C_1$-$C_4$alkyl), homoserine (optionally substituted with $C_1$-$C_4$alkyl, aryl, or ar$C_1$-$C_4$alkyl), tetrahydroisoquinoline-3-COOH, threonine (optionally substituted with $C_1$-$C_4$alkyl, aryl, or ar$C_1$-$C_4$alkyl), ornithine (optionally substituted with acyl, $C_1$-$C_4$alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently one or more of halogen, $C_1$-$C_4$alkyl, $C_1$-$C_4$alkoxy, hydroxy, $C_1$-$C_4$alkoxycarbonyl, amino, amidino, guanidino, fluorinated $C_1$-$C_4$alkyl, fluorinated $C_1$-$C_4$alkoxy, $C_1$-$C_4$alkylsulfonyl, $C_1$-$C_4$alkylcarbonyl, cyano, aryl, heteroaryl, ar$C_1$-$C_4$alkyl, $C_2$-$C_4$ alkenyl, alkynyl, or nitro;
$R_1$ and $R_2$ are each independently selected from the group consisting of hydrogen, $C_1$-$C_8$alkyl, ar($C_1$-$C_8$)alkyl, $C_1$-$C_8$alkoxycarbonyl, aryloxycarbonyl, ar($C_1$-$C_8$)alkoxycarbonyl, $C_1$-$C_8$alkylcarbonyl, arylcarbonyl, ar($C_1$-$C_8$)alkylcarbonyl, aminocarbonyl, $C_1$-$C_8$alkylaminocarbonyl, $C_1$-$C_8$dialkylaminocarbonyl, arylaminocarbonyl, diarylaminocarbonyl, ar($C_1$-$C_8$)alkylaminocarbonyl, diar($C_1$-$C_8$)alkylaminocarbonyl, heterocyclylcarbonyl, heteroaryl($C_1$-$C_8$)alkyl, heteroaryloxycarbonyl, heteroaryl($C_1$-$C_8$)alkoxycarbonyl, heteroarylcarbonyl, heteroaryl($C_1$-$C_8$)alkylcarbonyl, heteroarylaminocarbonyl, diheteroarylaminocarbonyl, heteroaryl($C_1$-$C_8$)alkylaminocarbonyl, and diheteroaryl-($C_1$-$C_8$)alkylaminocarbonyl wherein said aryl, ar($C_1$-$C_8$)alkyl, heteroaryl, and heteroaryl-($C_1$-$C_8$)alkyl are optionally substituted with one or more substituents which are halogen, $C_1$-$C_8$alkyl, $C_1$-$C_8$alkoxy, hydroxy, cyano, amino, or nitro;
$R_1$ and $R_2$ are covalently bonded to the N-terminus of $A_3$ when p is 1 or $A_2$ when p is 0;
$R_3$ is hydrogen or $C_1$-$C_8$alkyl;
$R_4$ is selected from the group consisting of unsubstituted or substituted aryl, ar$C_1$-$C_8$alkyl, $C_3$-$C_8$cycloalkyl, heteroaryl, and heteroaryl($C_1$-$C_8$)alkyl, where the substituents on the aryl, ar$C_1$-$C_8$alkyl, cycloalkyl, heteroaryl, or heteroaryl($C_1$-$C_8$)alkyl group are independently one or more of halogen, nitro, amino, cyano, hydroxyalkyl, $C_1$-$C_8$alkyl, $C_1$-$C_8$alkoxy, hydroxy, $C_1$-$C_4$alkylcarbonyl, $C_1$-$C_8$alkoxycarbonyl, fluorinated $C_1$-$C_4$alkyl, fluorinated $C_1$-$C_4$alkoxy, or $C_1$-$C_4$alkylsulfonyl;
$R_5$ is selected from the group consisting of amino, $C_1$-$C_8$alkylamino, $C_1$-$C_8$dialkyl-amino, arylamino, ar$C_1$-$C_8$alkylamino, $C_3$-$C_8$cycloalkylamino, heteroalkyl$C_1$-$C_8$alkylamino, heteroalkyl$C_1$-$C_8$alkyl-N-methylamino, $C_1$-$C_8$dialkylamino($C_1$-$C_8$)alkylamino, —N($C_1$-$C_8$alkyl)-$C_1$-$C_8$alkyl-N($C_1$-$C_8$alkyl)$_2$, —N($C_1$-$C_8$alkyl)($C_1$-$C_8$alkenyl), —N($C_1$-$C_8$alkyl)($C_3$-$C_8$cycloalkyl), heteroalkyl, and substituted heteroalkyl wherein the substituent on the heteroalkyl is oxo, amino, $C_1$-$C_8$alkoxy($C_1$-$C_8$)alkyl, $C_1$-$C_8$alkylamino, or $C_1$-$C_8$dialkylamino;
X is N or C;
Y is N, C, or —CO—;
provided that when Y is N, then X is C and there is a double bond between X and Y; provided also that when Y is C, then X is C and there is a double bond between X and Y; and provided also that when Y is —CO—, then X is N and there is a single bond between X and Y;
m is 0, 1, 2, or 3;
n is 1 or 2;
p is 0 or 1; and
enantiomers, diastereomers, tautomers, solvates, and pharmaceutically acceptable salts thereof.

3. A method of treating a condition mediated by thrombin receptor (PAR-1) in a subject in need thereof comprising administering to the subject a therapeutically effective amount of the compound of formula (I):

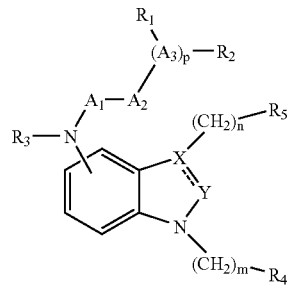

wherein
$A_1$, $A_2$ and $A_3$ are each independently a D- or L-amino acid selected from the group consisting of alanine, β-alanine, arginine, homoarginine, cyclohexylalanine, citrulline, cysteine (optionally substituted with $C_1$-$C_4$alkyl, aryl, or arC$_1$-C$_4$alkyl), 2,4-diaminobutyric acid (optionally substituted with acyl, C$_1$-C$_4$alkyl, aroyl, amidino, or MeC(NH)—), 2,3 diaminopropionic acid (optionally substituted with acyl, C$_1$-C$_4$alkyl, aroyl, amidino, or MeC(NH)—), glutamine, glycine, indanylglycine, lysine (optionally substituted with acyl, C$_1$-C$_4$alkyl, aroyl, MeC(NH)—), valine, methionine, proline, serine (optionally substituted with C$_1$-C$_4$alkyl, aryl, or arC$_1$-C$_4$alkyl), homoserine (optionally substituted with C$_1$-C$_4$alkyl, aryl, or arC$_1$-C$_4$alkyl), tetrahydroisoquinoline-3-COOH, threonine (optionally substituted with C$_1$-C$_4$alkyl, aryl, or arC$_1$-C$_4$alkyl), ornithine (optionally substituted with acyl, C$_1$-C$_4$alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently one or more of halogen, C$_1$-C$_4$alkyl, C$_1$-C$_4$alkoxy, hydroxy, C$_1$-C$_4$alkoxycarbonyl, amino, amidino, guanidino, fluorinated C$_1$-C$_4$alkyl, fluorinated C$_1$-C$_4$alkoxy, C$_1$-C$_4$alkylsulfonyl, C$_1$-C$_4$alkylcarbonyl, cyano, aryl, heteroaryl, arC$_1$-C$_4$alkyl, C$_2$-C$_4$ alkenyl, alkynyl, or nitro;

R$_1$ and R$_2$ are each independently selected from the group consisting of hydrogen, C$_1$-C$_8$alkyl, ar(C$_1$-C$_8$)alkyl, C$_1$-C$_8$alkoxycarbonyl, aryloxycarbonyl, ar(C$_1$-C$_8$)alkoxycarbonyl, C$_1$-C$_8$alkylcarbonyl, arylcarbonyl, ar(C$_1$-C$_8$)alkylcarbonyl, aminocarbonyl, C$_1$-C$_8$alkylaminocarbonyl, C$_1$-C$_8$dialkylaminocarbonyl, arylaminocarbonyl, diarylaminocarbonyl, ar(C$_1$-C$_8$)alkylaminocarbonyl, diar(C$_1$-C$_8$) alkylaminocarbonyl, heterocyclylcarbonyl, heteroaryl(C$_1$-C$_8$)alkyl, heteroaryloxycarbonyl, heteroaryl(C$_1$-C$_8$)alkoxycarbonyl, heteroarylcarbonyl, heteroaryl(C$_1$-C$_8$)alkylcarbonyl, heteroarylaminocarbonyl, diheteroarylaminocarbonyl, heteroaryl(C$_1$-C$_8$)alkylaminocarbonyl, and diheteroaryl-(C$_1$-C$_8$)alkylaminocarbonyl wherein said aryl, ar(C$_1$-C$_8$)alkyl, heteroaryl, and heteroaryl-(C$_1$-C$_8$)alkyl are optionally substituted with one or more substituents which are halogen, C$_1$-C$_8$alkyl, C$_1$-C$_8$alkoxy, hydroxy, cyano, amino, or nitro;

R$_1$ and R$_2$ are covalently bonded to the N-terminus of A$_3$ when p is 1 or A$_2$ when p is 0;

R$_3$ is hydrogen or C$_1$-C$_8$alkyl;

R$_4$ is selected from the group consisting of unsubstituted or substituted aryl, arC$_1$-C$_8$alkyl, C$_3$-C$_8$cycloalkyl, heteroaryl, and heteroaryl(C$_1$-C$_8$)alkyl, where the substituents on the aryl, arC$_1$-C$_8$alkyl, cycloalkyl, heteroaryl, or heteroaryl(C$_1$-C$_8$)alkyl group are independently one or more of halogen, nitro, amino, cyano, hydroxyalkyl, C$_1$-C$_8$alkyl, C$_1$-C$_8$alkoxy, hydroxy, C$_1$-C$_4$alkylcarbonyl, C$_1$-C$_8$alkoxycarbonyl, fluorinated C$_1$-C$_4$alkyl, fluorinated C$_1$-C$_4$alkoxy, or C$_1$-C$_4$alkylsulfonyl;

R$_5$ is selected from the group consisting of amino, C$_1$-C$_8$alkylamino, C$_1$-C$_8$dialkyl-amino, arylamino, arC$_1$-C$_8$alkylamino, C$_3$-C$_8$cycloalkylamino, heteroalkylC$_1$-C$_8$alkylamino, heteroalkylC$_1$-C$_8$alkyl-N-methylamino, C$_1$-C$_8$dialkylamino(C$_1$-C$_8$)alkylamino, —N(C$_1$-C$_8$alkyl)-C$_1$-C$_8$alkyl-N(C$_1$-C$_8$alkyl)$_2$, —N(C$_1$-C$_8$alkyl)(C$_1$-C$_8$alkenyl), —N(C$_1$-C$_8$alkyl)(C$_3$-C$_8$cycloalkyl), heteroalkyl, and substituted heteroalkyl wherein the substituent on the heteroalkyl is oxo, amino, C$_1$-C$_8$alkoxy(C$_1$-C$_8$)alkyl, C$_1$-C$_8$alkylamino, or C$_1$-C$_8$dialkylamino;

X is N or C;

Y is N, C, or —CO—;

provided that when Y is N, then X is C and there is a double bond between X and Y; provided also that when Y is C, then X is C and there is a double bond between X and Y; and provided also that when Y is —CO—, then X is N and there is a single bond between X and Y;

m is 0, 1, 2, or 3;

n is 1 or 2;

p is 0 or 1; and enantiomers, diastereomers, tautomers, solvates, and pharmaceutically acceptable salts thereof.

* * * * *

UNITED STATES PATENT AND TRADEMARK OFFICE
CERTIFICATE OF CORRECTION

| | | |
|---|---|---|
| PATENT NO. | : 7,618,945 B2 | |
| APPLICATION NO. | : 11/227504 | |
| DATED | : November 17, 2009 | |
| INVENTOR(S) | : Zhang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 225 days.

Signed and Sealed this

Twenty-sixth Day of October, 2010

David J. Kappos
*Director of the United States Patent and Trademark Office*